(12) United States Patent
Fischer et al.

(10) Patent No.: US 8,168,832 B2
(45) Date of Patent: May 1, 2012

(54) 2,4,6-TRIALKYLPHENYL SUBSTITUTED CYCLOPENTANE-1,3-DIONE

(75) Inventors: Reiner Fischer, Monheim (DE); Stefan Lehr, Liederbach (DE); Dieter Feucht, Eschborn (DE); Ulrich Görgens, Ratingen (DE); Olga Malsam, Rösrath (DE); Alfred Angermann, Kriftel (DE); Guido Bojack, Wiesbaden (DE); Alan Graff, Lörrach (DE); Christian Arnold, Langenfeld (DE); Thomas Auler, Leichlingen (DE); Martin Jeffrey Hills, Idstein (DE); Heinz Kehne, Hofheim (DE); Christopher Hugh Rosinger, Hofheim (DE); Jan Dittgen, Frankfurt (DE)

(73) Assignee: Bayer Cropscience AG, Monheim (DE)

( * ) Notice: Subject to any disclaimer, the term of this patent is extended or adjusted under 35 U.S.C. 154(b) by 782 days.

(21) Appl. No.: 12/159,967

(22) PCT Filed: Jan. 3, 2007

(86) PCT No.: PCT/EP2007/000023
§ 371 (c)(1),
(2), (4) Date: Nov. 17, 2008

(87) PCT Pub. No.: WO2007/080066
PCT Pub. Date: Jul. 19, 2007

(65) Prior Publication Data
US 2009/0137393 A1 May 28, 2009

(30) Foreign Application Priority Data
Jan. 7, 2006 (DE) .................. 10 2006 000 971

(51) Int. Cl.
C07C 49/00 (2006.01)
(52) U.S. Cl. ..................................... 568/329; 568/327
(58) Field of Classification Search ................ None
See application file for complete search history.

(56) References Cited

U.S. PATENT DOCUMENTS

| | | | |
|---|---|---|---|
| 4,021,224 A | 5/1977 | Pallos et al. | |
| 4,091,006 A | 5/1978 | Durden, Jr. et al. | |
| 4,186,130 A | 1/1980 | Teach | |
| 4,283,348 A | 8/1981 | Wheeler | |
| 4,338,122 A * | 7/1982 | Wheeler | 504/348 |
| 4,436,666 A | 3/1984 | Wheeler | |
| 4,526,723 A | 7/1985 | Wheeler et al. | |
| 4,551,547 A | 11/1985 | Wheeler | |
| 4,623,727 A | 11/1986 | Hubele | |
| 4,632,698 A | 12/1986 | Wheeler | |
| 4,639,266 A | 1/1987 | Heubach et al. | |
| 4,881,966 A | 11/1989 | Nyffeler et al. | |
| 4,891,057 A | 1/1990 | Sohn et al. | |
| 4,902,340 A | 2/1990 | Hubele | |
| 5,314,863 A | 5/1994 | Loher et al. | |
| 5,380,852 A | 1/1995 | Schutze et al. | |
| 5,401,700 A | 3/1995 | Sohn et al. | |
| 5,407,897 A | 4/1995 | Cary et al. | |
| 5,516,750 A | 5/1996 | Willms et al. | |
| 5,700,758 A | 12/1997 | Rosch et al. | |
| 5,739,079 A | 4/1998 | Holdgrun et al. | |
| 5,808,135 A | 9/1998 | Fischer et al. | |
| 5,840,661 A | 11/1998 | Fischer et al. | |
| 6,235,680 B1 | 5/2001 | Ziemer et al. | |
| 6,251,827 B1 | 6/2001 | Ziemer et al. | |
| 6,251,833 B1 | 6/2001 | Erdelen et al. | |
| 6,417,370 B1 | 7/2002 | Lieb et al. | |
| 6,451,843 B1 | 9/2002 | Lieb et al. | |
| 6,458,965 B1 | 10/2002 | Lieb et al. | |
| 6,511,940 B1 | 1/2003 | Ziemer et al. | |
| 6,515,184 B1 | 2/2003 | Fischer et al. | |
| 6,894,005 B1 | 5/2005 | Maetzke et al. | |
| 2003/0216260 A1 | 11/2003 | Ruther et al. | |
| 2005/0090399 A1 | 4/2005 | Friedmann et al. | |
| 2006/0166829 A1 | 7/2006 | Fischer et al. | |

FOREIGN PATENT DOCUMENTS

CA 2518620 A1 9/2004
EP 346620 A1 12/1989

OTHER PUBLICATIONS

Addition of Ammonium Sulfate (AMS), [online] 2003, Retrieved from the Internet: http://weeds.n msu.edu/pdfs/AMS_use.pdf>.*
Wolff (Burger's Medicinal Chemistry 4th Ed. Part I, New York, 1979, 336-337).*
International Search Report for PCT/EP07/00023, mailed Mar. 9, 2007.
Chambers, Mark S. et al, "An Asymmetric Synthesis of Thiotetronic Acids Using Chirality Transfer via an Allyl Xanthate-to-Dithiocarbonate Rearrangement. X-Ray Crystal Structure of (5R)-2,5-Dihydro-4-hydroxy-5-methyl-3-phenyl-5-prop-1'-eny1-2-oxothiophene," J. Chem. Soc. Chem. Commun., 1987, pp. 1228-1230.
Edwards, R.L. et al., "Constituents of the Higher Fungi. Part IV. Involutin, a Diphenylcyclopenteneone from *Paxillus involutus*," J. Chem. Soc., 1967, pp. 405-409.
Sousa, A.A. et al, "Esters of 3-Hydroxy-2-Arylindones, a New Class of Acaricide," J. of Economic Entomology, vol. 66, No. 2, 1973, pp. 584-586.
Micklefield, Jason et al., "Alkylation and Acylation of 5-Phenylsulphonyl- and 5-Cyanobutyrolactones," Tetrahedon, vol. 48, No. 36, 1992, pp. 7519-7526.

* cited by examiner

*Primary Examiner* — Daniel Sullivan
*Assistant Examiner* — Jennifer C Sawyer
(74) *Attorney, Agent, or Firm* — Baker Donelson Bearman, Caldwell & Berkowitz, PC

(57) ABSTRACT

The invention relates to novel 2,4,6-trialkylphenyl-substituted cyclopentane-1,3-diones of the formula (I)

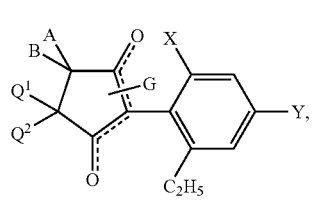

(I)

in which X, Y, A, B, $Q^1$, $Q^2$ and G have the meanings given above, to a plurality of processes and intermediates for their preparation and to their use as pesticides and/or herbicides, and also to selective herbicidal compositions comprising, firstly, the 2,4,6-trialkylphenyl-substituted cyclopentane-1,3-diones of the formula (I) and, secondly, at least one crop plant compatibility-improving compound.

17 Claims, No Drawings

2,4,6-TRIALKYLPHENYL SUBSTITUTED CYCLOPENTANE-1,3-DIONE

CROSS REFERENCE TO RELATED APPLICATIONS

This application is a §371 National Stage Application of PCT/EP2007/000023, filed Jan. 3, 2007, which claims priority to German Application 10 2006 000 971.1, filed Jan. 7, 2006, the content of which is incorporated by reference.

BACKGROUND OF THE INVENTION

1. Field of the Invention

The present invention relates to novel 2,4,6-trialkylphenyl-substituted cyclopentane-1,3-diones, to a plurality of processes for their preparation and to their use as pesticides and/or herbicides.

Moreover, the invention relates to novel selective herbicidal active compound combinations comprising, firstly, the 2,4,6-trialkylphenyl-substituted cyclopentane-1,3-dione derivatives and, secondly, at least one crop plant compatibility-improving compound, which combinations can be used with particularly good results for the selective control of weeds in various crops of useful plants.

2. Detailed Description of Related Art

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673, WO 01/17972, WO 01/74770, WO 03/062244, WO 04/080962, DE-A-10326386). Also known are compounds which are substituted in a similar way: 3-hydroxy-5,5-dimethyl-2-phenylcyclopent-2-en-1-one from the publication Micklefield et. al, Tetrahedron, (1992), 7519-26 and the natural product Involution (−)-cis-5-(3,4-dihydroxyphenyl)-3,4-dihydroxy-2-(4-hydroxyphenyl)cyclopent-2-enone from the publication Edwards et al., J. Chem. Soc. S, (1967), 405-9. An insecticidal or acaricidal action is not described. Moreover, 2-(2,4,6-trimethylphenyl)-1,3-indanedione is known from the publication J. Economic Entomology, 66 (1973), 584 and the laid-open publication DE-A 2 361 084, with herbicidal and acaricidal actions being stated.

However, in particular at low application rates and concentrations, the activity and activity spectrum of these compounds is not always fully satisfactory. Furthermore, the compatibility of these compounds with some crop plants is not always sufficient.

SUMMARY OF THE INVENTION

This invention now provides novel compounds of the formula (I)

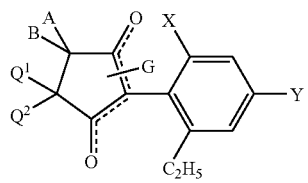

in which
X represents methyl and
Y represents methyl or ethyl, or
X and Y represent ethyl,
where
A represents hydrogen, in each case optionally halogen-substituted alkyl, alkenyl, alkoxyalkyl, alkylthioalkyl, saturated or unsaturated, optionally substituted cycloalkyl, in which optionally at least one ring atom is replaced by a heteroatom,
B represents hydrogen, alkyl or alkoxyalkyl, or
A and B together with the carbon atom to which they are attached represent a saturated or unsaturated unsubstituted or substituted cycle which optionally contains at least one heteroatom,
A and $Q^1$ together represent optionally substituted alkanediyl or alkenediyl which may optionally be interrupted by a heteroatom,
$Q^1$ and $Q^2$ independently of one another represent hydrogen or alkyl,
or in which
X represents ethyl
and
Y represents methyl,
where
A and B together with the carbon atom to which they are attached represent a saturated or unsaturated 4- to 8-membered unsubstituted or substituted cycle,
and
$Q^1$ and $Q^2$ represents hydrogen
or
A and $Q^1$ together represent in each case optionally substituted $C_2$-$C_6$-alkanediyl or $C_2$-$C_6$-alkenediyl which may optionally be interrupted by heteroatoms
and
B and $Q^2$ independently of one another represent hydrogen or alkyl,
G represents hydrogen (a) or represents one of the groups

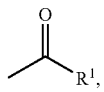

(b)

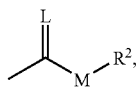

(c)

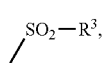

(d)

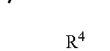

(e)

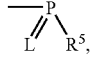

E or (f)

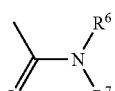

(g)

E represents a metal ion or an ammonium ion,
L represents oxygen or sulfur,
M represents oxygen or sulfur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulfur.

DETAILED DESCRIPTION OF A PREFERRED EMBODIMENT

Depending inter alia on the nature of the substituents, the compounds of the formula (I) may be present as geometric and/or optical isomers or isomer mixtures of varying composition which, if appropriate, may be separated in a customary manner. The present invention provides for the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having various proportions of isomeric compounds.

Depending on the position of the substituent G, the compounds of the formula (I) can be present in the two isomeric forms of the formulae (I-A) and (I-B),

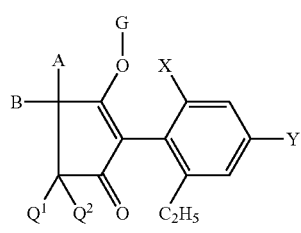
(I-A)

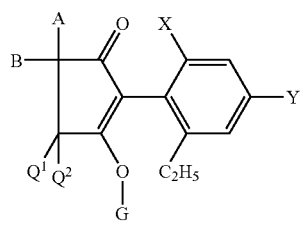
(I-B)

which is meant to be indicated by the broken line in formula (I).

The compounds of the formulae (I-A) and (I-B) can be present both as mixtures and in the form of their pure isomers. If appropriate, mixtures of the compounds of the formulae (I-A) and (I-B) can be separated by physical methods, for example by chromatographic methods.

For reasons of clarity, hereinbelow only one of the possible isomers is shown in each case. This does not exclude that, if appropriate, the compounds may be present in the form of the isomer mixtures or in the respective other isomeric form.

Including the different meanings (a), (b), (c), (d), (e), (f) and (g) of group G, the following principle structures (I-a) to (I-g) result:

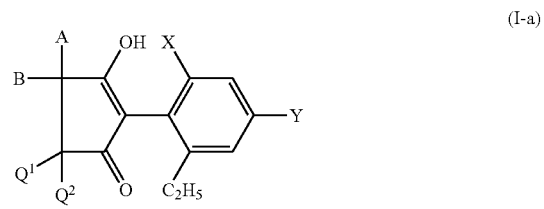
(I-a)

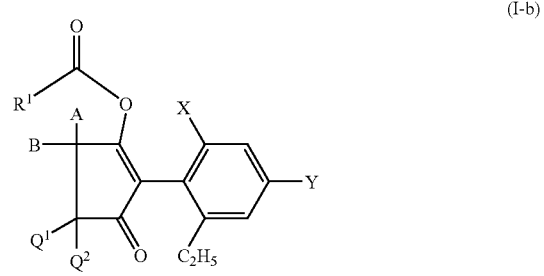
(I-b)

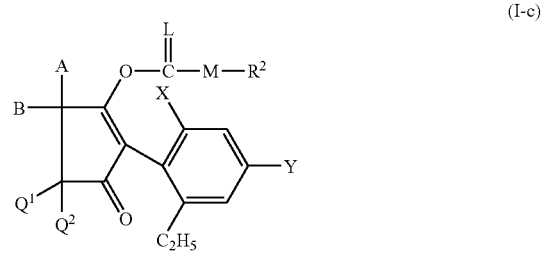
(I-c)

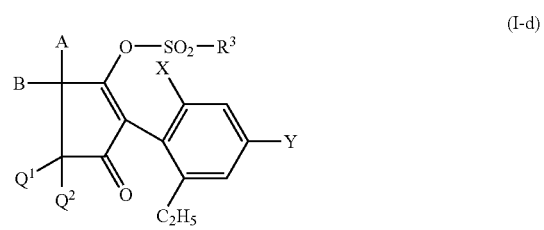
(I-d)

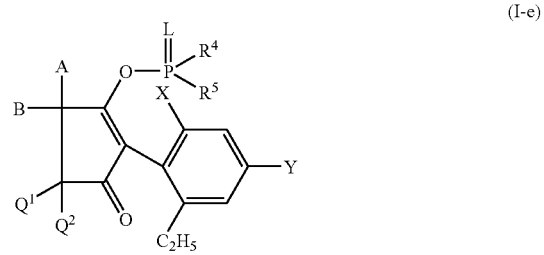
(I-e)

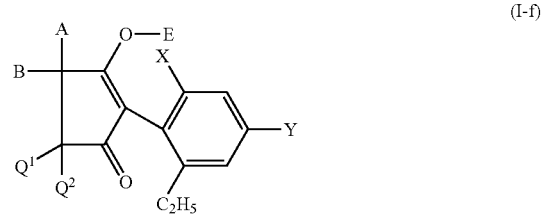
(I-f)

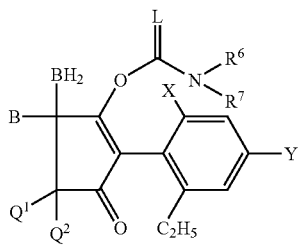

(I-g)

in which
A, B, $Q^1$, $Q^2$, E, L, M, X, Y, $R^1$, $R^2$, $R^3$, $R^4$, $R^5$, $R^6$ and $R^7$ have the meanings given above.

Furthermore, it has been found that the novel compounds of the formula (I) are obtained by the processes described below:

(A) Compounds of the formula (I-a)

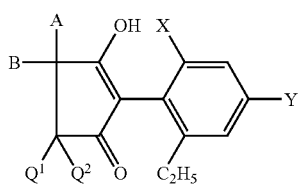

(I-a)

in which
A, B, $Q^1$, $Q^2$, X and Y have the meaning given above, are obtained when
ketocarboxylic esters of the formula (II)

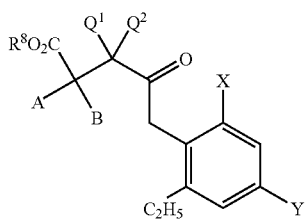

(II)

in which
A, B, $Q^1$, $Q^2$, X and Y have the meaning given above, and $R^8$ represents alkyl (in particular $C_1$-$C_8$-alkyl), are cyclized intramolecularly, if appropriate in the presence of a diluent and in the presence of a base.

Moreover, it has been found (B) that the compounds of the formula (I-b) shown above in which A, B, $Q^1$, $Q^2$, $R^1$, X, and Y have the meanings given above are obtained when compounds of the formula (I-a) shown above in which A, B, $Q^1$, $Q^2$, X and Y have the meanings given above, are in each case (α) reacted with acid halides of the formula (III)

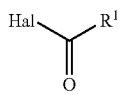

(III)

in which
$R^1$ has the meaning given above and
Hal represents halogen (in particular chlorine or bromine)
or (β) reacted with carboxylic anhydrides of the formula (IV)

$$R^1-CO-O-CO-R^1 \quad (IV)$$

in which
$R^1$ has the meaning given above,
if appropriate in the presence of a diluent and if appropriate in the presence of an acid binder;

(C) that the compounds of the formula (I-c) shown above in which A, B, $Q^1$, $Q^2$, $R^2$, M, X and Y have the meanings given above and L represents oxygen are obtained when compounds of the formula (I-a) shown above in which A, B, $Q^1$, $Q^2$, X and Y have the meanings given above are in each case reacted with chloroformic esters or chloroformic thioesters of the formula (V)

$$R^2\text{-M-CO-Cl} \quad (V)$$

in which
$R^2$ and M have the meanings given above,
if appropriate in the presence of a diluent and if appropriate in the presence of an acid binder;

(D) that compounds of the formula (I-c) shown above in which A, B, $Q^1$, $Q^2$, $R^2$, M, X and Y have the meanings given above and L represents sulfur are obtained when compounds of the formula (I-a) shown above in which A, B, D, $Q^1$, $Q^2$, X and Y have the meanings given above are in each case reacted with chloromonothioformic esters or chlorodithioformic esters of the formula (VI)

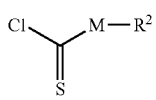

(VI)

in which
M and $R^2$ have the meanings given above,
if appropriate in the presence of a diluent and if appropriate in the presence of an acid binder
and (E) that compounds of the formula (I-d) shown above in which A, B, $Q^1$, $Q^2$, $R^3$, X and Y have the meanings given above are obtained when compounds of the formula (I-a) shown above in which A, B, D, $Q^1$, $Q^2$, X and Y have the meanings given above are in each case reacted with sulfonyl chlorides of the formula (VII)

$$R^3-SO_2-Cl \quad (VII)$$

in which
$R^3$ has the meaning given above,
if appropriate in the presence of a diluent and if appropriate in the presence of an acid binder, (F) that compounds of the formula (I-e) shown above in which A, B, L, $Q^1$, $Q^2$, $R^4$, $R^5$, X and Y have the meanings given above are obtained when compounds of the formula (I-a) shown above in which A, B, $Q^1$, $Q^2$, X and Y have the meanings given above are in each case reacted with phosphorus compounds of the formula (VIII)

(VIII)

in which

L, $R^4$ and $R^5$ have the meanings given above and

Hal represents halogen (in particular chlorine or bromine), if appropriate in the presence of a diluent and if appropriate in the presence of an acid binder, (G) that compounds of the formula (I-f) shown above in which A, B, E, $Q^1$, $Q^2$, X and Y have the meanings given above are obtained when compounds of the formula (I-a) in which A, B, $Q^1$, $Q^2$, X and Y have the meanings given above are in each case reacted with metal compounds or amines of the formulae (IX) and (X), respectively $$Me(OR^{10})_t$$ (IX)

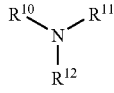

(X)

in which

Me represents a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (H) that compounds of the formula (I-g) shown above in which A, B, L, $Q^1$, $Q^2$, $R^6$, $R^7$, X and Y have the meanings given above are obtained when compounds of the formula (I-a) shown above in which A, B, $Q^1$, $Q^2$, X and Y have the meanings given above are in each case (α) reacted with isocyanates or isothiocyanates of the formula (XI)

$$R^6-N=C=L$$ (XI)

in which $R^6$ and L have the meanings given above, if appropriate in the presence of a diluent and if appropriate in the presence of a catalyst or (β) reacted with carbamoyl chlorides or thiocarbamoyl chlorides of the formula (XII)

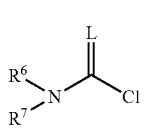

(XII)

in which

L, $R^6$ and $R^7$ have the meanings given above, if appropriate in the presence of a diluent and if appropriate in the presence of an acid binder.

Furthermore, it has been found that the novel compounds of the formula (I) are very effective as pesticides, preferably as insecticides, acaricides and herbicides.

Surprisingly, it has now also been found that certain substituted cyclic ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soya beans and rice.

The invention also provides selective herbicidal compositions comprising an effective amount of an active compound combination comprising, as components, a') at least one compound of the formula (I) in which A, B, G, $Q^1$, $Q^2$, X and Y have the meaning given above and (b') at least one crop plant compatibility-improving compound from the following group of compounds:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N, N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5- methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzenesulphonamide, and/or one of the following compounds, defined by general formulae of the general formula (IIa)

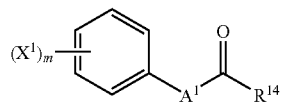
(IIa)

or of the general formula (IIb)

(IIb)

or of the formula (IIc)

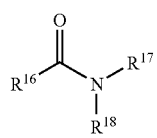
(IIc)

where m represents a number 0, 1, 2, 3, 4 or 5, $A^1$ represents one of the divalent heterocyclic groupings shown below

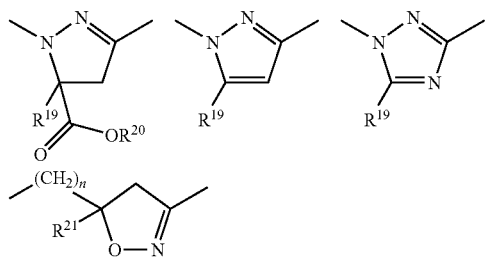

n represents a number 0, 1, 2, 3, 4 or 5, $A^2$ represents optionally $C_1$-$C_4$-alkyl- and/or $C_1$-$C_4$-alkoxycarbonyl- and/or $C_1$-$C_4$-alkenyloxycarbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae of the general formula (IId)

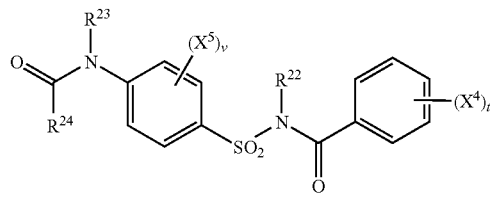

or of the general formula (IIe)

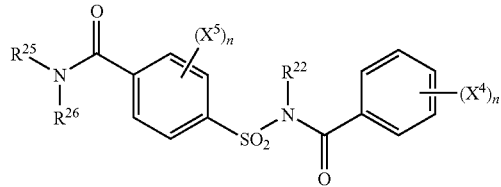

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae mentioned above and below are illustrated below:

X preferably represents methyl and

Y preferably represents methyl or ethyl or

X and Y both preferably represent ethyl,

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulfur, B preferably represents hydrogen, $C_1$-$C_{12}$-alkyl or $C_1$-$C_8$-alkoxy-$C_1$-$C_6$-alkyl or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulfur and which are optionally mono- or disubstituted by $C_1$-$C_8$-alkyl, $C_1$-$C_8$-haloalkyl or $C_1$-$C_8$-alkoxy or A, B and the carbon atom to which they are attached preferably represent $C_3$-$C_6$-cycloalkyl which is substituted by an alkylenediyl group which is optionally substituted by $C_1$-$C_4$-alkyl and optionally contains one or two not directly adjacent oxygen and/or sulfur atoms, or by an alkylenedioxyl or by an alkylenedithioyl group which, together with the carbon atom to which it is attached, forms a further five- to eight-membered ring or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanediyl, $C_2$-$C_6$-alkenediyl in which optionally one methylene group is replaced by oxygen or sulfur, A and $Q^1$ together preferably represent $C_2$-$C_6$-alkanediyl or $C_2$-$C_6$-alkenediyl, each of which is optionally mono- or disubstituted by identical or different substituents from the group consisting of halogen, hydroxyl, of $C_1$-$C_{10}$-alkyl, $C_1$-$C_6$-alkoxy, $C_1$-$C_6$-alkylthio, $C_3$-$C_7$-cycloalkyl, each of which is optionally mono- to trisubstituted by identical or different halogen, and of benzyloxy or phenyl, each of which is optionally mono- to trisubstituted by identical or different halogen, $C_1$-$C_6$-alkyl or $C_1$-$C_6$-alkoxy, where each $C_2$-$C_6$-alkanediyl and $C_2$-$C_6$-alkenediyl group furthermore optionally contains one of the groups below

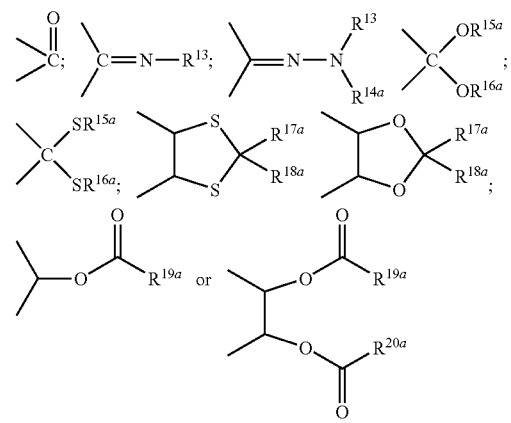

or is bridged by a $C_1$-$C_2$-alkanediyl group or interrupted or bridged by an oxygen atom, $Q^1$ and $Q^2$ independently of one another preferably represent hydrogen or $C_1$-$C_4$-alkyl, or X preferably represents ethyl and Y preferably represents methyl and a) A, B and the carbon atom to which they are attached preferably represent saturated $C_4$-$C_8$-cycloalkyl or unsaturated $C_5$-$C_8$-cycloalkyl in which optionally one ring member is replaced by oxygen or sulfur and which are optionally mono- or disubstituted by $C_1$-$C_8$-alkyl, $C_1$-$C_8$-haloalkyl or $C_1$-$C_8$-alkoxy or A, B and the carbon atom to which they are attached preferably represent $C_3$-$C_6$-cycloalkyl which is substituted by an alkylenediyl group which is optionally substituted by $C_1$-$C_4$-alkyl and optionally contains one or two not directly adjacent oxygen and/or sulfur atoms, or by an alkylenedioxyl or by an alkylenedithioyl group which, together with the carbon atom to which it is attached, forms a further five- to eight-membered ring or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulfur, $Q^1$ and $Q^2$ preferably represent hydrogen, or b) A and $Q^1$ together preferably represent $C_2$-$C_6$-alkanediyl or $C_2$-$C_6$-alkenediyl, each of which is optionally mono- or disubstituted by identical or different substituents from the group consisting of halogen, hydroxyl, of $C_1$-$C_{10}$-alkyl, $C_1$-$C_6$-alkoxy, $C_1$-$C_6$-alkylthio, $C_3$-$C_7$-cycloalkyl, each of which is optionally mono- to trisubstituted by identical or different halogen, and of benzyloxy or phenyl, each of which is optionally mono- to trisubstituted by identical or different halogen, $C_1$-$C_6$-alkyl or $C_1$-$C_6$-alkoxy, where each $C_2$-$C_6$-alkanediyl and $C_2$-$C_6$-alkenediyl group furthermore optionally contains one of the groups below

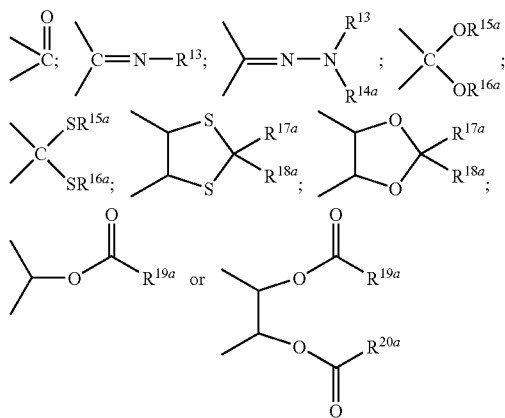

or is bridged by a $C_1$-$C_2$-alkanediyl group or interrupted or bridged by an oxygen atom, B and $Q^2$ independently of one another preferably represent hydrogen or $C_1$-$C_2$-alkyl, G preferably represents hydrogen (a) or represents one of the groups

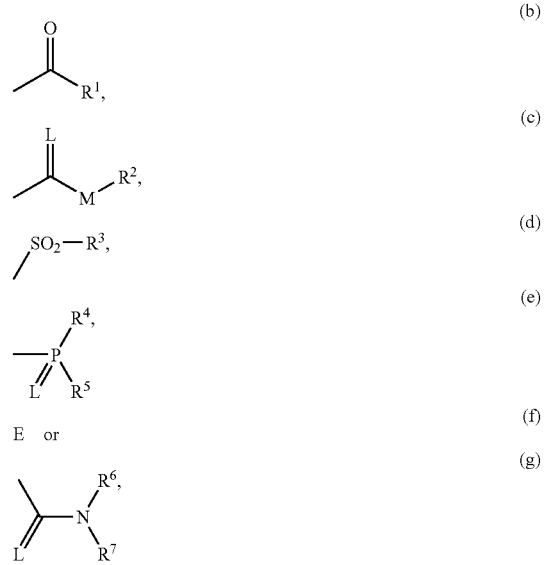

in particular (a), (b), (c) or (g)

in which

E represents a metal ion equivalent or an ammonium ion,

L represents oxygen or sulfur and

M represents oxygen or sulfur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulfur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ preferably independently of one another represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulfur, $R^{13}$ preferably represents hydrogen, represents in each case optionally halogen-substituted $C_1$-$C_8$-alkyl, $C_1$-$C_8$-alkoxy or $C_3$-$C_8$-alkenyloxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulfur or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, hetaryl, phenyl-$C_1$-$C_4$-alkyl, phenyl-$C_1$-$C_4$-alkoxy or hetaryl-$C_1$-$C_4$-alkoxy, $R^{14a}$ preferably represents hydrogen or $C_1$-$C_8$-alkyl or $R^{13}$ and $R^{14a}$ together preferably represent $C_4$-$C_6$-alkanediyl, $R^{15a}$ and $R^{16a}$ are identical or different and preferably represent $C_1$-$C_6$-alkyl or $R^{15a}$ and $R^{16a}$ together preferably represent a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulfur, $R^{19a}$ and $R^{20a}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di($C_1$-$C_{10}$-alkyl)amino or di($C_3$-$C_{10}$-alkenyl)amino.

In the radical definitions mentioned as being preferred, halogen represents fluorine, chlorine, bromine and iodine, in particular fluorine, chlorine and bromine.

X particularly preferably represents methyl,
Y particularly preferably represents methyl or ethyl or
X and Y both particularly preferably represent ethyl,
A particularly preferably represents hydrogen, represents $C_1$-$C_6$-alkyl, $C_1$-$C_4$-alkoxy-$C_1$-$C_2$-alkyl, each of which is optionally mono- to trisubstituted by fluorine or chlorine or represents $C_3$-$C_6$-cycloalkyl which is optionally mono- or disubstituted by $C_1$-$C_2$-alkyl or $C_1$-$C_2$-alkoxy, B particularly preferably represents hydrogen, $C_1$-$C_4$-alkyl or $C_1$-$C_2$-alkoxy-$C_1$-$C_2$-alkyl or A, B and the carbon atom to which they are attached particularly preferably represent saturated or unsaturated $C_5$-$C_7$-cycloalkyl in which optionally one ring member is replaced by oxygen or sulfur and which is optionally mono- or disubstituted by $C_1$-$C_6$-alkyl, trifluoromethyl or $C_1$-$C_6$-alkoxy, A, B and the carbon atom to which they are attached particularly preferably represent $C_5$-$C_6$-cycloalkyl which is substituted by an alkylenediyl group which is optionally substituted by methyl or ethyl and optionally contains one or two not directly adjacent oxygen and/or sulfur atoms, or by an alkylenedioxyl or by an alkylenedithioyl group which, together with the carbon atom to which it is attached, forms a further five- or six-membered ring, A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, A and $Q^1$ together particularly preferably represent $C_3$-$C_4$-alkanediyl or $C_3$-$C_4$-alkenediyl, each of which is optionally mono- or disubstituted by identical or different substituents from the group consisting of hydroxyl, $C_1$-$C_2$-alkyl and $C_1$-$C_2$-alkoxy and which optionally contains one of the groups below

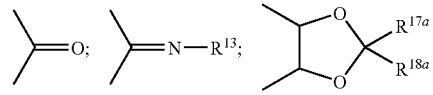

or may be interrupted or bridged by an oxygen atom, $Q^1$ and $Q^2$ independently of one another particularly preferably represent hydrogen or $C_1$-$C_2$-alkyl or X particularly preferably represents ethyl
and
Y particularly preferably represents methyl
and a) A, B and the carbon atom to which they are attached particularly preferably represent saturated or unsaturated $C_5$-$C_7$-cycloalkyl in which optionally one ring member is replaced by oxygen or sulfur and which is optionally mono- or disubstituted by $C_1$-$C_6$-alkyl, trifluoromethyl or $C_1$-$C_6$-alkoxy, with the proviso that in this case $Q^3$ particularly preferably represents hydrogen or methyl, or A, B and the carbon atom to which they are attached particularly preferably represent $C_5$-$C_6$-cycloalkyl which is substituted by an alkylenediyl group which is optionally substituted by methyl or ethyl and optionally contains one or two not directly adjacent oxygen and/or sulfur atoms, or by an alkylenedioxyl or by an alkylenedithioyl group which, together with the carbon atom to which it is attached, forms a further five- or six-membered ring, with the proviso that in this case $Q^3$ particularly preferably represents hydrogen or methyl, A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, with the proviso that in this case $Q^3$ particularly preferably represents hydrogen or methyl, or $Q^1$ and $Q^2$ particularly preferably represent hydrogen or b) A and $Q^1$ together particularly preferably represent $C_3$-$C_4$-alkanediyl or $C_3$-$C_4$-alkenediyl, each of which is optionally mono- or disubstituted by identical or different substituents from the group consisting of hydroxyl, $C_1$-$C_2$-alkyl and $C_1$-$C_{12}$-alkoxy and which optionally contains one of the groups below

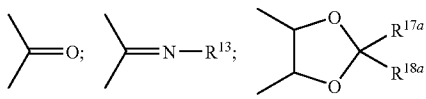

or is interrupted or bridged by an oxygen atom,

B and $Q^2$ independently of one another particularly preferably represent hydrogen or methyl, G particularly preferably represents hydrogen (a) or represents one of the groups

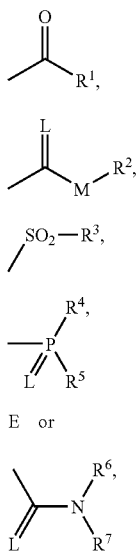

in particular (a), (b) or (c), in which

E represents a metal ion equivalent or an ammonium ion,

L represents oxygen or sulfur and

M represents oxygen or sulfur, $R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-alkyl or $C_1$-$C_2$-alkoxy or represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_6$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio, $C_3$-$C_4$-alkenylthio, $C_3$-$C_6$-cycloalkylthio, each of which is optionally mono- to trisubstituted by fluorine or chlorine, or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ particularly preferably represents $C_1$-$C_6$-alkoxy or $C_1$-$C_6$-alkylthio which is optionally monosubstituted by chlorine, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ particularly preferably together represent a $C_4$-$C_5$-alkylene radical which is optionally substituted by methyl or ethyl and in which optionally one methylene group is replaced by oxygen or sulfur, $R^{13}$ particularly preferably represents hydrogen, represents $C_1$-$C_8$-alkyl, $C_1$-$C_8$-alkoxy, $C_3$-$C_6$-alkenyloxy, each of which is optionally mono- to trisubstituted by fluorine or chlorine, represents $C_3$-$C_8$-cycloalkyl which is optionally substituted by halogen, $C_1$-$C_4$-alkyl or $C_1$-$C_4$-alkoxy and in which optionally one methylene group is replaced by oxygen or sulfur, or represents phenyl, pyridyl, pyrimidyl, thiazolyl, phenyl-$C_1$-$C_2$-alkyl or pyridyl-$C_1$-$C_2$-alkoxy, each of which is optionally substituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $R^{17a}$ and $R^{18a}$ independently of one another particularly preferably represent hydrogen, represent $C_1$-$C_4$-alkyl which is optionally mono- to trisubstituted by fluorine or chlorine or represent phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano or $R^{17a}$ and $R^{18a}$ together with the carbon atom to which they are attached particularly preferably represent a carbonyl group or represent $C_5$-$C_6$-cycloalkyl which is optionally mono- or disubstituted by fluorine, chlorine, $C_1$-$C_3$-alkyl or $C_1$-$C_4$-alkoxy.

In the radical definitions mentioned as being particularly preferred, halogen represents fluorine, chlorine and bromine, in particular fluorine and chlorine.

X very particularly preferably represents methyl,

Y very particularly preferably represents methyl or ethyl or

X and Y both very particularly preferably represent ethyl,

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl, B very particularly preferably represents hydrogen, methyl or ethyl or A, B and the carbon atom to which they are attached very particularly preferably represent saturated $C_5$-$C_6$-cycloalkyl in which optionally one ring member is replaced by oxygen and which is optionally monosubstituted by methyl, ethyl, propyl, isopropyl, trifluoromethyl, methoxy, ethoxy, propoxy or butoxy, A, B and the carbon atom to which they are attached very particularly preferably represent $C_6$-cycloalkyl which is substituted by an alkylenedioxyl group which contains two not directly adjacent oxygen atoms and which, together with the carbon atom to which it is attached, forms a further five- or six-membered ring, A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, A and $Q^1$ together very particularly preferably represent $C_3$-$C_4$-alkanediyl or $C_3$-$C_4$-alkenediyl, each of which is optionally mono- or disubstituted by identical or different substituents from the group consisting of hydroxyl, methyl and methoxy and which optionally contain one of the groups below

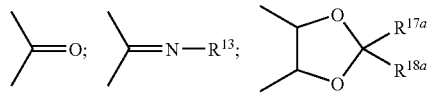

or may be interrupted or bridged by an oxygen atom, $Q^1$ and $Q^2$ independently of one another very particularly preferably represent hydrogen or methyl or X very particularly preferably represents ethyl and Y very particularly preferably represents methyl and a) A, B and the carbon atom to which they are attached very particularly preferably represent saturated $C_5$-$C_6$-cycloalkyl in which optionally one ring member is replaced by oxygen or sulfur and which is optionally monosubstituted by methyl, ethyl, propyl, isopropyl, trifluoromethyl, methoxy, ethoxy, propoxy or butoxy, A, B and the carbon atom to which they are attached very particularly preferably represent $C_6$-cycloalkyl which is substituted by an alkylenedioxyl group which contains two not directly adjacent oxygen atoms and which, together with the carbon atom to which it is attached, forms a further five- or six-membered ring, A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, $Q^1$ and $Q^2$ very particularly preferably represent hydrogen or b) A and $Q^1$ together very particularly preferably represent $C_3$-$C_4$-alkanediyl or $C_3$-$C_4$-alkenediyl, each of which is optionally mono- or disubstituted by identical or different substituents from the group consisting of hydroxyl, methyl and methoxy and which optionally contain one of the groups below

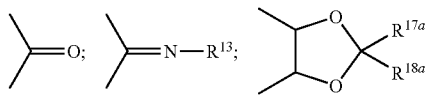

or is interrupted or bridged by an oxygen atom,

B and $Q^2$ very particularly preferably independently of one another represent hydrogen or methyl, G very particularly preferably represents hydrogen (a) or represents one of the groups

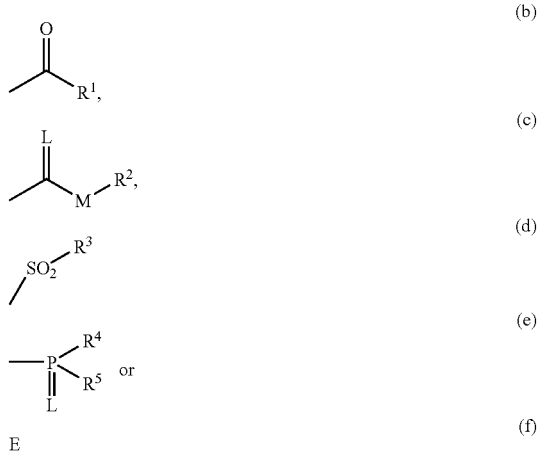

in which

E represents an ammonium ion,

L represents oxygen or sulfur and

M represents oxygen or sulfur, $R^1$ very particularly preferably represents $C_1$-$C_6$-alkyl, $C_2$-$C_6$-alkenyl, $C_1$-$C_2$-alkoxy-$C_1$—alkyl, $C_1$-$C_2$-alkylthio-$C_1$-alkyl or represents $C_3$-$C_6$-cyclopropyl which is optionally monosubstituted by fluorine, chlorine, methyl or methoxy or represents $C_1$-$C_4$-alkyl which is monosubstituted by chlorine, represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally mono- to trisubstituted by fluorine, $R^3$ very particularly preferably represents $C_1$-$C_6$-alkyl, $R^4$ very particularly preferably represents $C_1$-$C_4$-alkyl, $C_1$-$C_4$-alkoxy, $C_1$-$C_4$-alkylamino, di($C_1$-$C_4$-alkyl)amino, $C_1$-$C_4$-alkylthio, $C_3$-$C_4$-alkenylthio, $C_3$-$C_6$-cycloalkylthio, each of which is optionally mono- to trisubstituted by fluorine or chlorine, or represents phenyl, phenoxy or phenylthio, each of which is optionally monosubstituted by fluorine, chlorine, bromine, nitro, cyano, methoxy, trifluoromethoxy, methylthio, trifluoromethylthio, methyl or trifluoromethyl, $R^5$ very particularly preferably represents $C_1$-$C_4$-alkoxy or $C_1$-$C_4$-alkylthio which is optionally monosubstituted by chlorine, $R^{13}$ very particularly preferably represents $C_1$-$C_4$-alkyl, $C_1$-$C_4$-alkoxy or $C_3$-$C_4$-alkenyloxy, each of which is optionally mono- to trisubstituted by fluorine or chlorine, or represents benzyl or pyridyl, each of which is optionally substituted by fluorine, chlorine, bromine, methyl, methoxy, trifluoromethyl or trifluoromethoxy, $R^{17a}$ and $R^{18a}$ independently of one another very particularly preferably represent $C_1$-$C_4$-alkyl which is optionally mono- to trisubstituted by fluorine or chlorine, or represent phenyl which is optionally mono- or disubstituted by fluorine, chlorine, bromine, methyl, methoxy, trifluoromethyl, trifluoromethoxy, nitro or cyano or $R^{17a}$ and $R^{18a}$ together with the carbon atom to which they are attached very particularly preferably represent $C_5$-$C_6$-cycloalkyl which is optionally mono- or disubstituted by methyl or ethyl.

X most preferably represents methyl,
Y most preferably represents methyl or ethyl
or
X and Y both most preferably represent ethyl,
A most preferably represents methyl,
B most preferably represents hydrogen or methyl or
A, B and the carbon atom to which they are attached most preferably represent saturated $C_5$-$C_6$-cycloalkyl in which optionally one ring member is replaced by oxygen and which is optionally monosubstituted by methyl,
A and $Q^1$ together most preferably represent $C_3$-$C_5$-alkanediyl or $C_3$-$C_5$-alkenediyl, each of which is optionally monosubstituted by methyl,
which optionally contain one of the groups below

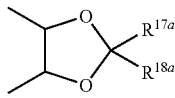

$Q^1$ and $Q^2$ most preferably represent hydrogen,
or
X most preferably represents ethyl
and
Y most preferably represents methyl
and
a) A, B and the carbon atom to which they are attached most preferably represent saturated $C_5$-$C_6$-cycloalkyl in which optionally one ring member is replaced by oxygen,
$Q^1$ and $Q^2$ most preferably represent hydrogen
or
b) A and $Q^1$ together most preferably represent $C_3$-$C_5$-alkanediyl or $C_3$-$C_5$-alkenediyl, each of which is optionally monosubstituted by methyl,
which optionally contain one of the groups below

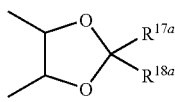

or are interrupted or bridged by an oxygen atom,

B and $Q^2$ most preferably represent hydrogen,
G most preferably represents hydrogen (a) or represents one of the groups

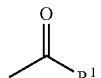
(b)

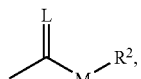
(c)

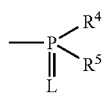
(e)

in which
L represents oxygen and
M represents oxygen,
$R^1$ most preferably represents $C_1$-$C_6$-alkyl, $C_1$-$C_2$-alkoxy-$C_1$-$C_2$-alkyl, or represents $C_1$-$C_4$-alkyl which is monosubstituted by chlorine,
$R^2$ most preferably represents $C_1$-$C_8$-alkyl,
$R^4$ most preferably represents $C_1$-$C_4$-alkoxy which is optionally monosubstituted by chlorine,
$R^5$ most preferably represents $C_1$-$C_4$-alkoxy which is optionally monosubstituted by chlorine,
$R^{17a}$ and $R^{18a}$ most preferably represent methyl.

Especially preferred are the isomerically pure compounds of the formula (I') in which
X and Y independently of one another represent methyl or ethyl,
and
G represents the very particularly preferred radicals,

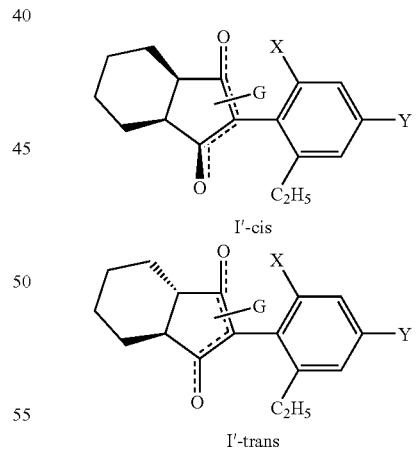

I'-cis

I'-trans where particular emphasis is given to the trans compounds.

The general or preferred radical definitions listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Optionally substituted radicals may be mono- or polysubstituted unless indicated otherwise, and in the case of multiple substitutions the substituents can be identical or different.

In addition to the compounds mentioned in the examples, the following compounds of the formula (I-1-a) may be specifically mentioned:

TABLE 1

[Structure: cyclopentanone fused with phenyl ring bearing OH, X, Y, $C_2H_5$ substituents; A, B, $Q^1$, $Q^2$ positions shown]

$X = CH_3$, $Y = CH_3$, $Q^2 = H$

| A | B | $Q^1$ |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| cyclopropyl | $CH_3$ | H |
| cyclopentylmethyl | $CH_3$ | H |
| cyclohexylmethyl | $CH_3$ | H |
| —(CH$_2$)$_2$— | | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |

TABLE 1-continued

[Same structure as above]

$X = CH_3$, $Y = CH_3$, $Q^2 = H$

| A | B | $Q^1$ |
|---|---|---|
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CHi—C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHOi—C$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |

| A | $Q^1$ | B |
|---|---|---|
| —(CH$_2$)$_3$— | | H |
| —(CH$_2$)$_4$— | | H |
| —CH$_2$—CH$_2$—CHCH$_3$—CH$_2$— | | H |
| —CH$_2$—CH$_2$—CH$_2$—CHCH$_3$— | | H |
| —CH$_2$—CHCH$_3$—CHCH$_3$—CH$_2$— | | H |
| —CH$_2$—CH=CH—CH$_2$— | | H |
| —(CH$_2$)$_4$— | | $CH_3$ |
| —CH$_2$—CH(–O–)CH—CH$_2$— (epoxide) | | H |
| —CH$_2$—CH(–O–C(CH$_3$)$_2$–O–)CH—CH$_2$— | | H |
| —CH$_2$—CH(–O–CH$_2$–O–)CH—CH$_2$— | | H |

TABLE 2

[Same general structure]

$X = C_2H_5$, $Y = C_2H_5$, $Q^2 = H$

| A | B | $Q^1$ |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |

TABLE 2-continued

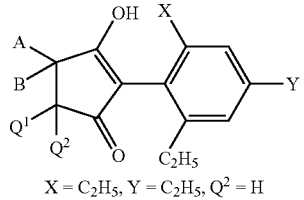

X = C$_2$H$_5$, Y = C$_2$H$_5$, Q$^2$ = H

| A | B | Q$^1$ |
|---|---|---|
| t-C$_4$H$_9$ | CH$_3$ | H |
| C$_2$H$_5$ | C$_2$H$_5$ | H |
| C$_3$H$_7$ | C$_3$H$_7$ | H |
| cyclopropyl | CH$_3$ | H |
| cyclopentyl | CH$_3$ | H |
| cyclohexyl | CH$_3$ | H |
| —(CH$_2$)$_2$— | | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CHi—C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHOi-C$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |

| A | Q$^1$ | B |
|---|---|---|
| —(CH$_2$)$_3$— | | H |
| —(CH$_2$)$_4$— | | H |
| —CH$_2$—CH$_2$—CHCH$_3$—CH$_2$— | | H |
| —CH$_2$—CH$_2$—CH$_2$—CHCH$_3$— | | H |
| —CH$_2$—CHCH$_3$—CHCH$_3$—CH$_2$— | | H |
| —CH$_2$—CH=CH—CH$_2$— | | H |
| —(CH$_2$)$_4$— | | CH$_3$ |
| —CH$_2$—CH(O)CH—CH$_2$— (epoxide) | | H |
| —CH$_2$—CH—CH—CH$_2$— (with dioxolane C(CH$_3$)$_2$) | | H |
| —CH$_2$—CH—CH—CH$_2$— (with dioxolane OCH$_2$O) | | H |

TABLE 3

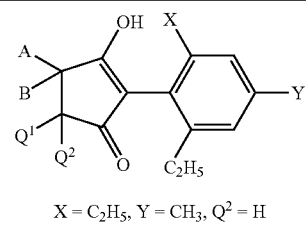

X = C$_2$H$_5$, Y = CH$_3$, Q$^2$ = H

| A | B | Q$^1$ |
|---|---|---|
| CH$_3$ | H | H |
| C$_2$H$_5$ | H | H |
| C$_3$H$_7$ | H | H |
| i-C$_3$H$_7$ | H | H |
| C$_4$H$_9$ | H | H |
| i-C$_4$H$_9$ | H | H |
| s-C$_4$H$_9$ | H | H |
| t-C$_4$H$_9$ | H | H |
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| C$_4$H$_9$ | CH$_3$ | H |
| i-C$_4$H$_9$ | CH$_3$ | H |
| s-C$_4$H$_9$ | CH$_3$ | H |
| t-C$_4$H$_9$ | CH$_3$ | H |
| C$_2$H$_5$ | C$_2$H$_5$ | H |
| C$_3$H$_7$ | C$_3$H$_7$ | H |
| cyclopropyl | CH$_3$ | H |
| cyclopentyl | CH$_3$ | H |
| cyclohexyl | CH$_3$ | H |
| —(CH$_2$)$_2$— | | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CHi-C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHOi-C$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |

| A | Q$^1$ | B |
|---|---|---|
| —(CH$_2$)$_3$— | | H |
| —(CH$_2$)$_4$— | | H |
| —CH$_2$—CH$_2$—CHCH$_3$—CH$_2$— | | H |
| —CH$_2$—CH$_2$—CH$_2$—CHCH$_3$— | | H |
| —CH$_2$—CHCH$_3$—CHCH$_3$—CH$_2$— | | H |
| —CH$_2$—CH=CH—CH$_2$— | | H |
| —CH$_2$—CH(O)CH—CH$_2$— (epoxide) | | H |

TABLE 3-continued

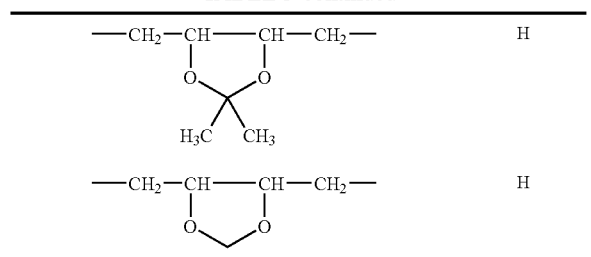

| | |
|---|---|
| —CH$_2$—CH—CH—CH$_2$— (with O-C(CH$_3$)$_2$-O bridge) | H |
| —CH$_2$—CH—CH—CH$_2$— (with O-CH$_2$-O bridge) | H |

Preferred meanings of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

$A^1$ preferably represents one of the divalent heterocyclic groupings shown below

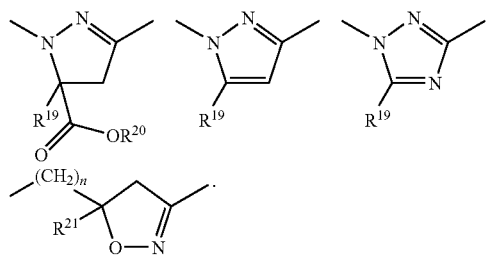

n preferably represents the numbers 0, 1, 2, 3 or 4.

$A^2$ preferably represents in each case optionally methyl-, ethyl-, methoxycarbonyl-, ethoxycarbonyl-, or alkyloxycarbonyl-substituted methylene or ethylene.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents in each case optionally fluorine-, chlorine- and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl.

$R^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with $R^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2, 3, or 4.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

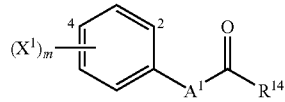

(IIa)

| Example No. | (Positions) $(X^1)_m$ | $A^1$ | $R^{14}$ |
|---|---|---|---|
| IIa-1 | (2) Cl, (4) Cl | [pyrazoline with H3C, CO-OCH3] | OCH$_3$ |
| IIa-2 | (2) Cl, (4) Cl | [pyrazoline with H3C, CO-OC2H5] | OCH$_3$ |
| IIa-3 | (2) Cl, (4) Cl | [pyrazoline with H3C, CO-OCH3] | OC$_2$H$_5$ |
| IIa-4 | (2) Cl, (4) Cl | [pyrazoline with H3C, CO-OC2H5] | OC$_2$H$_5$ |
| IIa-5 | (2) Cl | [pyrazole with phenyl] | OCH$_3$ |
| IIa-6 | (2) Cl, (4) Cl | [pyrazole with phenyl] | OCH$_3$ |
| IIa-7 | (2) F | [pyrazole with phenyl] | OCH$_3$ |
| IIa-8 | (2) F | [pyrazole with 2-Cl-phenyl] | OCH$_3$ |
| IIa-9 | (2) Cl, (4) Cl | [triazole with Cl$_3$C] | OC$_2$H$_5$ |
| IIa-10 | (2) Cl, (4) CF$_3$ | [triazole with phenyl] | OCH$_3$ |
| IIa-11 | (2) Cl | [pyrazole with 2-F-phenyl] | OCH$_3$ |

TABLE-continued

Examples of the compounds of the formula (IIa)

(IIa)

| Example No. | (Positions) $(X^1)_m$ | $A^1$ | $R^{14}$ |
|---|---|---|---|
| IIa-12 | — | (methyl-phenyl-isoxazoline) | $OC_2H_5$ |
| IIa-13 | (2) Cl, (4) Cl | (1-methyl-3-methyl-pyrazole) | $OC_2H_5$ |
| IIa-14 | (2) Cl, (4) Cl | (1-methyl-3-isopropyl-pyrazole) | $OC_2H_5$ |
| IIa-15 | (2) Cl, (4) Cl | (1-methyl-3-tert-butyl-pyrazole) | $OC_2H_5$ |
| IIa-16 | (2) Cl, (4) Cl | (ethyl-methyl-isoxazoline) | $OC_2H_5$ |
| IIa-17 | (2) Cl, (4) Cl | (methyl-isoxazoline) | $OC_2H_5$ |
| IIa-18 | — | (methyl-phenyl-isoxazoline) | OH |

Examples of the compounds of the formula (IIb) which are very particularly preferred as herbicide safeners according to the invention are listed in the table below.

TABLE

Examples of the compounds of the formula (*IIb)

(IIb)

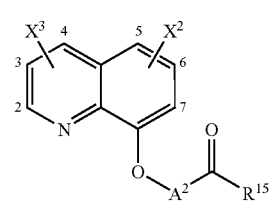

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7\text{-n}$ |
| IIb-5 | (5) Cl | — | $CH_2$ | $OC_3H_7\text{-i}$ |
| IIb-6 | (5) Cl | — | $CH_2$ | $OC_4H_9\text{-n}$ |
| IIb-7 | (5) Cl | — | $CH_2$ | $OCH(CH_3)C_5H_{11}\text{-n}$ |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH{=}CH_2$ |
| IIb-11 | (5) Cl | — | $CH_2$ | $OC_4H_9\text{-i}$ |
| IIb-12 | (5) Cl | — | $CH_2$ | (allyloxy-methoxy-propyl group) |
| IIb-13 | (5) Cl | — | $CH(CH_2)$ (=CH_2) allyl | $OCH_2CH{=}CH_2$ with isobutyryl |
| IIb-14 | (5) Cl | — | $C_2H_5$ CH | $OC_2H_5$ with isobutyryl |
| IIb-15 | (5) Cl | — | $CH_3$ CH | $OCH_3$ with isobutyryl |

Examples of the compounds of the formula (IIc) which are very particularly preferred as herbicide safeners according to the invention are listed in the table below.

TABLE

Examples of the compounds of the formula (IIc)

(IIc)

$R^{16}-C(=O)-N(R^{17})(R^{18})$

| Example No. | $R^{16}$ | $N(R^{17}, R^{18})$ |
|---|---|---|
| IIc-1 | $CHCl_2$ | $N(CH_2CH{=}CH_2)_2$ |
| IIc-2 | $CHCl_2$ | (2,2,3-trimethyl-oxazolidine) |

Examples of the compounds of the formula (IIc)

(IIc) structure: $R^{16}-C(=O)-N(R^{17})(R^{18})$

| Example No. | $R^{16}$ | $N(R^{17}, R^{18})$ |
|---|---|---|
| IIc-3 | CHCl₂ | 2,2-dimethyl-4-methyl-oxazolidine (N-methyl, with H₃C, CH₃ on C2 and CH₃ on C4) |
| IIc-4 | CHCl₂ | 1-oxa-4-azaspiro[4.5]decane (N-methyl spiro cyclohexane oxazolidine) |
| IIc-5 | CHCl₂ | 2,2-dimethyl-5-phenyl-oxazolidine (N-methyl, 2,2-diCH₃, 5-C₆H₅) |
| IIc-6 | CHCl₂ | 3-methyl-3,4-dihydro-2H-benzo[b][1,4]oxazine (N-methyl) |
| IIc-7 | CHCl₂ | 2,2-dimethyl-5-(furan-2-yl)-oxazolidine (N-methyl) |

Examples of the compounds of the formula (IId) which are very particularly preferred as herbicide safeners according to the invention are listed in the table below.

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | CH₃ | (2) OCH₃ | — |
| IId-2 | H | H | C₂H₅ | (2) OCH₃ | — |
| IId-3 | H | H | C₃H₇-n | (2) OCH₃ | — |
| IId-4 | H | H | C₃H₇-i | (2) OCH₃ | — |
| IId-5 | H | H | cyclopropyl | (2) OCH₃ | — |
| IId-6 | H | H | CH₃ | (2) OCH₃ (5) CH₃ | — |
| IId-7 | H | H | C₂H₅ | (2) OCH₃ (5) CH₃ | — |
| IId-8 | H | H | C₃H₇-n | (2) OCH₃ (5) CH₃ | — |
| IId-9 | H | H | C₃H₇-i | (2) OCH₃ (5) CH₃ | — |
| IId-10 | H | H | cyclopropyl | (2) OCH₃ (5) CH₃ | — |
| IId-11 | H | H | OCH₃ | (2) OCH₃ (5) CH₃ | — |
| IId-12 | H | H | OC₂H₅ | (2) OCH₃ (5) CH₃ | — |
| IId-13 | H | H | OC₃H₇-i | (2) OCH₃ (5) CH₃ | — |
| IId-14 | H | H | SCH₃ | (2) OCH₃ (5) CH₃ | — |
| IId-15 | H | H | SC₂H₅ | (2) OCH₃ (5) CH₃ | — |
| IId-16 | H | H | SC₃H₇-i | (2) OCH₃ (5) CH₃ | — |
| IId-17 | H | H | NHCH₃ | (2) OCH₃ (5) CH₃ | — |
| IId-18 | H | H | NHC₂H₅ | (2) OCH₃ (5) CH₃ | — |
| IId-19 | H | H | NHC₃H₇-i | (2) OCH₃ (5) CH₃ | — |
| IId-20 | H | H | NH-cyclopropyl (N-methyl) | (2) OCH₃ (5) CH₃ | — |
| IId-21 | H | H | NHCH₃ | (2) OCH₃ | — |
| IId-22 | H | H | NHC₃H₇-i | (2) OCH₃ | — |
| IId-23 | H | H | N(CH₃)₂ | (2) OCH₃ | — |
| IId-24 | H | H | N(CH₃)₂ | (3) CH₃ (4) CH₃ | — |
| IId-25 | H | H | CH₂—O—CH₃ | (2) OCH₃ | — |

Examples of the compounds of the formula (IIe) which are very particularly preferred as herbicide safeners according to the invention are listed in the table below.

TABLE

Examples of the compounds of the formula (IIe)

(IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H |  | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | (cyclopropyl) | (2) $OCH_3$ (5) $CH_3$ | — |
| IIe-12 | H | $CH_3$ | $CH_3$ | (2) $OCH_3$ (5) $CH_3$ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

Examples of the selective herbicidal combinations according to the invention comprising in each case one active compound of the formula (I) and one of the safeners defined above are listed in the table below.

TABLE

Examples of combinations according to the invention

| Active compounds of the formula (I) | Safener |
|---|---|
| I-a | cloquintocet-mexyl |
| I-a | fenchlorazole-ethyl |
| I-a | isoxadifen-ethyl |
| I-a | mefenpyr-diethyl |
| I-a | furilazole |
| I-a | fenclorim |
| I-a | cumyluron |
| I-a | daimuron/dymron |
| I-a | dimepiperate |
| I-a | IIe-11 |
| I-a | IIe-5 |
| I-b | cloquintocet-mexyl |
| I-b | fenchlorazole-ethyl |
| I-b | isoxadifen-ethyl |
| I-b | mefenpyr-diethyl |
| I-b | furilazole |
| I-b | fenclorim |
| I-b | cumyluron |
| I-b | daimuron/dymron |
| I-b | dimepiperate |
| I-b | IIe-11 |
| I-b | IIe-5 |
| I-c | cloquintocet-mexyl |
| I-c | fenchlorazole-ethyl |
| I-c | isoxadifen-ethyl |
| I-c | mefenpyr-diethyl |
| I-c | furilazole |
| I-c | fenclorim |
| I-c | cumyluron |
| I-c | daimuron/dymron |
| I-c | dimepiperate |
| I-c | IIe-11 |
| I-c | IIe-5 |
| I-d | cloquintocet-mexyl |
| I-d | fenchlorazole-ethyl |
| I-d | isoxadifen-ethyl |
| I-d | mefenpyr-diethyl |
| I-d | furilazole |
| I-d | fenclorim |
| I-d | cumyluron |
| I-d | daimuron/dymron |
| I-d | dimepiperate |
| I-d | IIe-11 |
| I-d | IIe-5 |
| I-e | cloquintocet-mexyl |
| I-e | fenchlorazole-ethyl |
| I-e | isoxadifen-ethyl |
| I-e | mefenpyr-diethyl |
| I-e | furilazole |
| I-e | fenclorim |
| I-e | cumyluron |
| I-e | daimuron/dymron |
| I-e | dimepiperate |
| I-e | IIe-11 |
| I-e | IIe-5 |
| I-f | cloquintocet-mexyl |
| I-f | fenchlorazole-ethyl |
| I-f | isoxadifen-ethyl |
| I-f | mefenpyr-diethyl |
| I-f | furilazole |
| I-f | fenclorim |
| I-f | cumyluron |
| I-f | daimuron/dymron |
| I-f | dimepiperate |
| I-f | IIe-5 |
| I-f | IIe-11 |
| I-g | cloquintocet-mexyl |
| I-g | fenchlorazole-ethyl |
| I-g | isoxadifen-ethyl |
| I-g | mefenpyr-diethyl |
| I-g | furilazole |
| I-g | fenclorim |
| I-g | cumyluron |
| I-g | daimuron/dymron |
| I-g | dimepiperate |
| I-g | IIe-5 |
| I-g | IIe-11 |

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Surprisingly, it has now been found that the active compound combinations, defined above, of compounds of the general formula (I) and safeners (antidotes) from group (b') listed above, while being very well tolerated by useful plants, have a particularly high herbicidal activity and can be used in various crops, in particular in cereals (especially wheat), but also in soya beans, potatoes, maize and rice, for the selective control of weeds.

Here, it has to be considered surprising that, from a large number of known safeners or antidotes capable of antagonizing the harmful effect of a herbicide on crop plants, those suitable are in particular the compounds of group (b') listed above which eliminate the harmful effect of compounds of the formula (I) on the crop plants virtually completely without having a major adverse effect on the herbicidal activity against the weeds.

Emphasis may be given here to the particularly advantageous effect of the particularly and most preferred combination partners from group (b'), in particular with respect to sparing cereal plants, such as, for example, wheat, barley and rye, but also maize and rice, as crop plants.

Using, for example, according to process (A) ethyl 5-(2-ethyl-4,6-dimethylphenyl)-2,3-tetramethylene-4-oxovalerate, the course of the process according to the invention can be represented by the reaction scheme below:

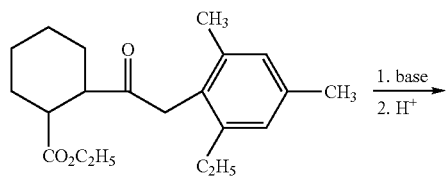

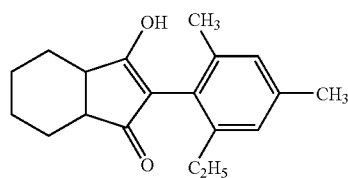

Using, for example, according to process (B) 2-(2-ethyl-4, 6-dimethylphenyl)-4,4-dimethylcyclopentane-1,3-dione and pivaloyl chloride as starting materials, the course of the process according to the invention can be represented by the reaction scheme below:

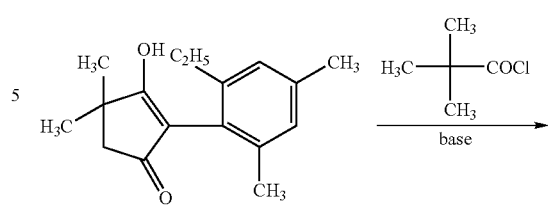

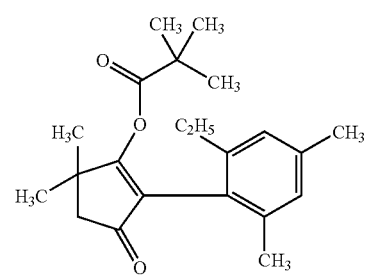

Using, for example, according to process (B) 2-(2,6-diethyl-4-methylphenyl)-4,4-pentamethylene-1,3-dione and acetic anhydride as starting materials, the course of the process according to the invention can be represented by the reaction scheme below:

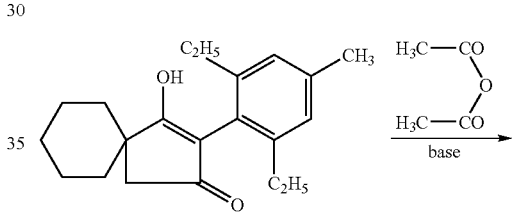

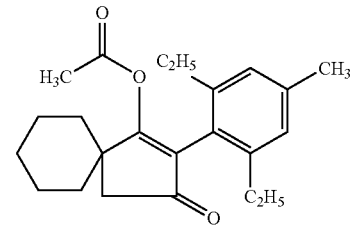

Using, for example, according to process (C) 2-[(2,6-diethyl-4-methyl)phenyl]-4,5-tetramethylenecyclopentane-1, 3-dione and ethyl chloroformate as starting materials, the course of the process according to the invention can be represented by the reaction scheme below:

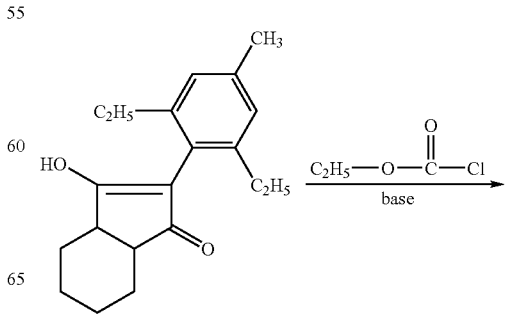

-continued

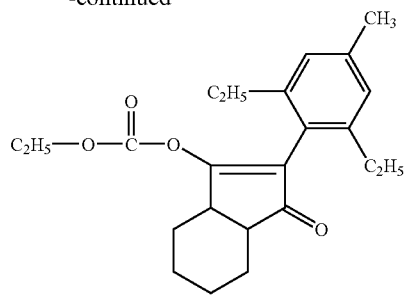

Using, for example, according to process (D) 2-[(2,4,6-triethylphenyl]-4,5-tetramethylenecyclopentane-1,3-dione and methyl chloromonothioformate as starting materials, the course of the process according to the invention can be represented by the reaction scheme below:

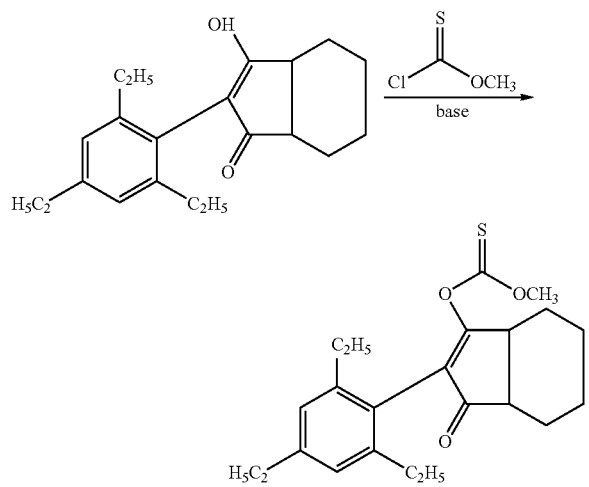

Using, for example, according to process (E) 2-(2,6-diethyl-4-methylphenyl)-5,5-pentamethylenecyclopentane-1,3-dione and methanesulphonyl chloride as starting material, the course of the reaction can be represented by the reaction scheme below:

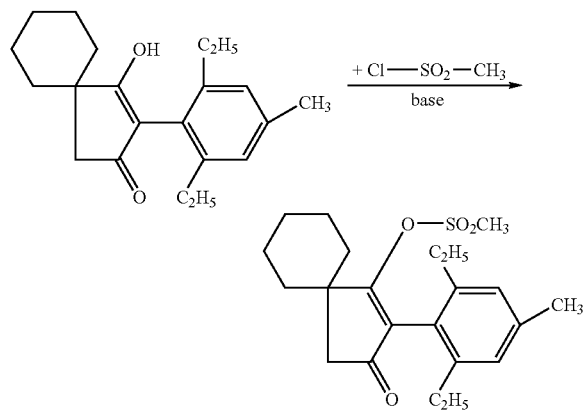

Using, for example, according to process (F) 2-(2-ethyl-4,6-dimethylphenyl)-4,4-dimethylcyclopentane-1,3-dione and 2,2,2-trifluoroethyl methanethiophosphonate as starting materials, the course of the reaction can be represented by the reaction scheme below:

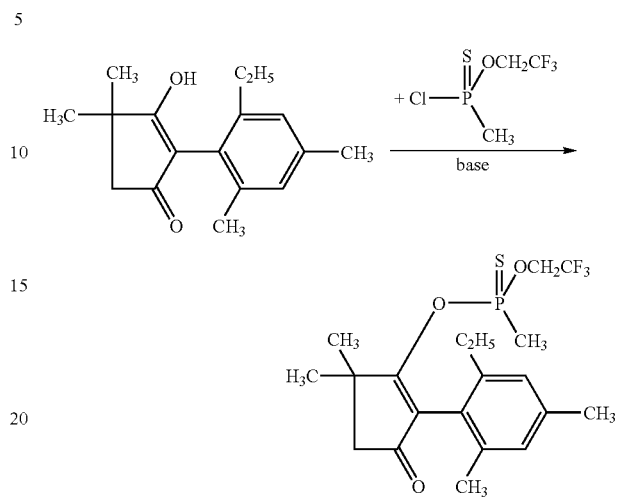

Using, for example, according to process (G) 2-(2-ethyl-4,6-dimethylphenyl)-4,4-dimethylcyclopentane-1,3-dione and NaOH as components, the course of the process according to the invention can be represented by the reaction scheme below:

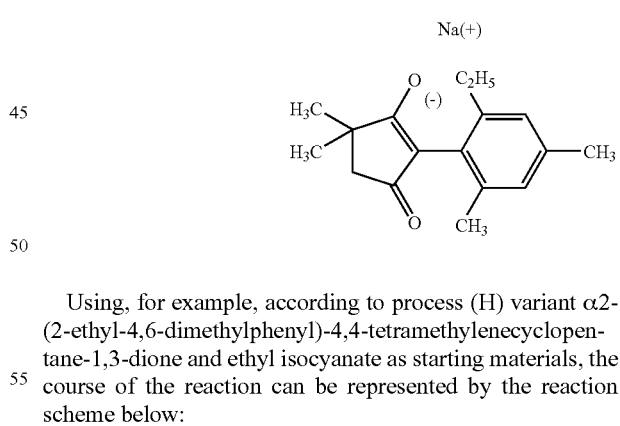

Using, for example, according to process (H) variant α2-(2-ethyl-4,6-dimethylphenyl)-4,4-tetramethylenecyclopentane-1,3-dione and ethyl isocyanate as starting materials, the course of the reaction can be represented by the reaction scheme below:

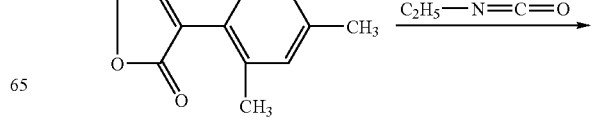

-continued

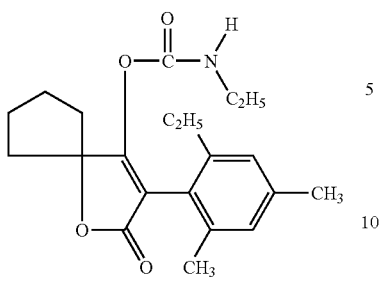

Using, for example, according to process (H) variant β2-(2,6-diethyl-4-methylphenyl)-5,5-pentamethylenecyclopentane-1,3-dione and dimethylcarbamoyl chloride as starting materials, the course of the reaction can be represented by the reaction scheme below:

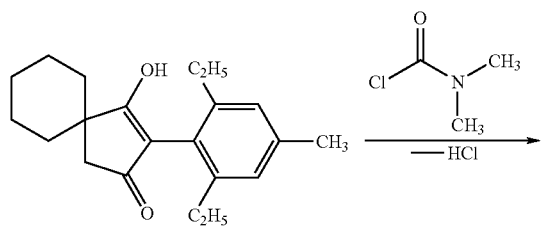

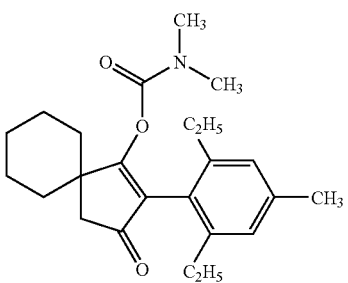

The compounds, required as starting materials in process (A) according to the invention, of the formula (II)

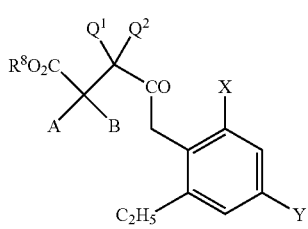

(II)

in which

A, B, $Q^1$, $Q^2$, X, Y and $R^8$ have the meaning given above, are novel.

They can be prepared by methods known in principle.

The 5-aryl-4-ketocarboxylic esters of the formula (II) are obtained, for example, when 5-aryl-4-ketocarboxylic acids of the formula (XIII)

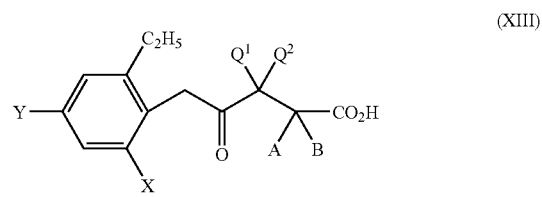

(XIII)

in which

X, Y, A, B, $Q^1$ and $Q^2$ have the meaning given above, are esterified (cf., for example, Organikum, 15. edition, Berlin, 1977, page 499) or alkylated (see Preparation Example).

The 5-aryl-4-ketocarboxylic acids of the formula (XIII)

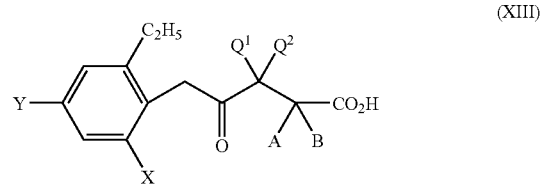

(XIII)

in which

A, B, $Q^1$, $Q^2$, X and Y have the meaning given above, are novel, but can be prepared by methods known in principle (WO 96/01 798, WO 97/14667, WO 98/39281, WO 01/74770).

The 5-aryl-4-ketocarboxylic acids of the formula (XIII) are obtained, for example, when 2-phenyl-3-oxoadipic esters of the formula (XIV)

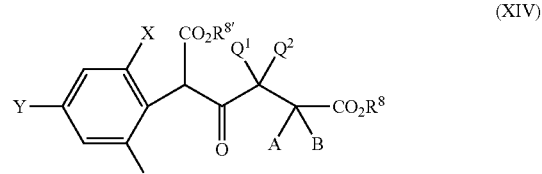

(XIV)

in which

A, B, $Q^1$, $Q^2$, X and Y have the meaning given above and $R^8$ and $R^{8'}$ represent alkyl (in particular $C_1$-$C_8$-alkyl) and, when the compound of the formula (XVI) is used, $R^8$ represents hydrogen, are decarboxylated, if appropriate in the presence of a diluent and if appropriate in the presence of a base or an acid (cf., for example, Organikum, 15. edition, Berlin, 1977, pages 519 to 521).

The compounds of the formula (XIV)

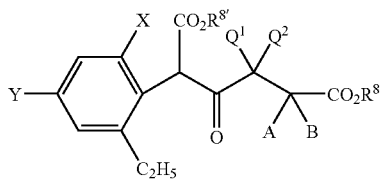

in which
A, B, $Q^1$, $Q^2$, X, Y, $R^8$, $R^{8'}$ have the meaning given above and, when the compound of the formula (XVI) is used, $R^8$ represents hydrogen,
are novel.

The compounds of the formula (XIV) are obtained, for example,
when dicarboxylic monoester chlorides of the formula (XV),

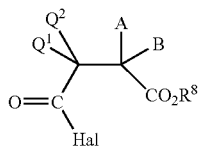

in which
A, B, $Q^1$, $Q^2$ and $R^8$ have the meaning given above and
Hal represents chlorine or bromine,
or carboxylic anhydrides of the formula (XVI)

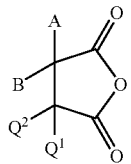

in which
A, B, $Q^1$ and $Q^2$ have the meaning given above,
are acylated with a phenylacetic ester of the formula (XVII)

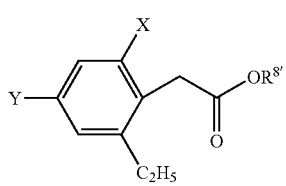

in which
X, Y and $R^{8'}$ have the meaning given above,
in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XV) and (XVI) are known compounds of organic chemistry, and/or they can be prepared in a simple manner by methods known in principle.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formulae (IX) and (X) and isocyanates of the formula (XI) and carbamoyl chlorides of the formula (XII) furthermore required as starting materials for carrying out the processes (B), (C), (D), (E), (F), (G) and (H) according to the invention are generally known compounds of organic or inorganic chemistry.

In addition, the compounds of the formulae (XV), (XVI) and (XVII) are known from the patent applications cited at the outset and/or can be prepared by the methods given therein.

The process (A) is characterized in that compounds of the formula (II) in which A, B, $Q^1$, $Q^2$, X, Y and $R^8$ have the meanings given above are subjected to an intramolecular condensation in the presence of a base.

Suitable diluents for use in the process (A) according to the invention are all organic solvents inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, molar amounts. However, it is also possible to use a relatively large excess (up to 3 mol) of one component or the other.

The process (B-α) is characterized in that compounds of the formula (I-a) are in each case reacted with carbonyl halides of the formula (III), if appropriate in the presence of a diluent and if appropriate in the presence of an acid binder.

Suitable diluents for use in the process (B-α) according to the invention are all solvents inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulfoxide and sulfolane. If the acid halide is sufficiently stable to hydrolysis, the reaction can also be carried out in the presence of water.

Suitable acid binders for the reaction according to process (B-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (B-α) according to the invention can be varied within a relatively wide range. In general, the process is carried out at temperatures between −20° C. and +150° C., preferably between 0° C. and 100° C.

When carrying out the process (B-α) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process (B-β) is characterized in that compounds of the formula (I-a) are reacted with carboxylic anhydrides of the formula (IV), if appropriate in the presence of a diluent and if appropriate in the presence of an acid binder.

Suitable diluents for use in the process (B-β) according to the invention are, preferably, the diluents which are also preferred when using acid halides. Besides, excess carboxylic anhydride may simultaneously act as diluent.

Suitable acid binders, which are added, if appropriate, for process (B-β) are, preferably, the acid binders which are also preferred when using acid halides.

The reaction temperatures in the process (B-β) according to the invention may be varied within a relatively wide range. In general, the process is carried out at temperatures between −20° C. and +150° C., preferably between 0° C. and 100° C.

When carrying out the process (B-β) according to the invention, the starting materials of the formula (I-a) and the carboxylic anhydride of the formula (IV) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (C) is characterized in that compounds of the formula (I-a) are in each case reacted with chloroformic esters or chloroformic thioesters of the formula (V), if appropriate in the presence of a diluent and if appropriate in the presence of an acid binder.

Suitable acid binders for the process (C) according to the invention are all customary acid acceptors. Preference is given to using tertiary amines, such as triethylamine, pyridine, DABCO, DBU, DBN, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (C) according to the invention are all solvents which are inert towards the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane.

When carrying out the process (C) according to the invention, the reaction temperatures can be varied within a relatively wide range. If the reaction is carried out in the presence of a diluent and of an acid binder, the reaction temperatures are generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thioester of the formula (III) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (D) according to the invention is characterized in that compounds of the formula (I-a) are in each case reacted with compounds of the formula (VI) in the presence of a diluent and, if appropriate, in the presence of an acid binder.

In preparation process (D), about 1 mol of chloromonothioformic ester or chlorodithioformic ester of the formula (VI) is employed per mole of the starting material of the formula (I-a) at from 0 to 120° C., preferably from 20 to 60° C.

Suitable diluents which are added, if appropriate, are all inert polar organic solvents, such as ethers, amides, sulfones, sulfoxides, and also halogenated alkanes.

Preference is given to using dimethyl sulfoxide, tetrahydrofuran, dimethylformamide or methylene chloride.

If, in a preferred embodiment, the enolate salt of the compounds (I-a) is prepared by addition of strong deprotonating agents, such as, for example, sodium hydride or potassium tert-butoxide, the further addition of acid binders may be dispensed with.

If acid binders are used, these may be customary inorganic or organic bases, for example sodium hydroxide, sodium carbonate, potassium carbonate, pyridine, triethylamine.

The reaction may be carried out at atmospheric pressure or under elevated pressure and is preferably carried out at atmospheric pressure. Work-up is carried out by customary methods.

The process (E) according to the invention is characterized in that compounds of the formula (I-a) are in each case reacted with sulfonyl chlorides of the formula (VII), if appropriate in the presence of a diluent and if appropriate in the presence of an acid binder.

In preparation process (E), about 1 mol of sulfonyl chloride of the formula (VII) is reacted per mole of the starting material of the formula (I-a), at from −20 to 150° C., preferably from 20 to 70° C.

Suitable diluents which are added, if appropriate, are all inert polar organic solvents, such as ethers, amides, nitriles, sulfones, sulfoxides or halogenated hydrocarbons, such as methylene chloride.

Preference is given to using dimethyl sulfoxide, tetrahydrofuran, dimethylformamide, methylene chloride.

If, in a preferred embodiment, the enolate salt of the compounds (I-a) is prepared by addition of strongly deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction may be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with phosphorus compounds of the formula (VIII), if appropriate in the presence of a diluent and if appropriate in the presence of an acid binder.

In preparation process (F), to obtain compounds of the formula (I-e), from 1 to 2, preferably from 1 to 1.3, mol of the phosphorus compound of the formula (VIII) are reacted per mole of the compounds (I-a), at temperatures between −40° C. and 150° C., preferably between −10 and 110° C.

Suitable diluents which are added, if appropriate, are all inert polar organic solvents, such as ethers, amides, nitrites, alcohols, sulphides, sulphones, sulphoxides etc.

Preference is given to using acetonitrile, dimethyl sulfoxide, tetrahydrofuran, dimethylformamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The end products are preferably purified by crystallization, chromatographic purification or "incipient distillation", i.e. removal of the volatile components under reduced pressure.

The process (G) is characterized in that compounds of the formula (I-a) are reacted with metal hydroxides or metal alkoxides of the formula (IX) or amines of the formula (X), if appropriate in the presence of a diluent.

Suitable diluents for use in the process (G) according to the invention are, preferably, ethers, such as tetrahydrofuran, dioxane, diethyl ether, or else alcohols, such as methanol, ethanol, isopropanol, and also water.

The process (G) according to the invention is generally carried out under atmospheric pressure.

The reaction temperatures are generally between −20° C. and 100° C., preferably between 0° C. and 50° C.

The process (H) according to the invention is characterized in that compounds of the formula (I-a) are in each case reacted with (H-α) compounds of the formula (XI), if appropriate in the presence of a diluent and if appropriate in the presence of a catalyst, or (H-β) with compounds of the formula (XII), if appropriate in the presence of a diluent and if appropriate in the presence of an acid binder.

In preparation process (H-α) about 1 mol of isocyanate of the formula (XI) is reacted per mole of starting material of the formula (I-a), at from 0 to 100° C., preferably from 20 to 50° C.

Suitable diluents which are added, if appropriate, are all inert organic solvents, such as ethers, amides, nitriles, sulphones, sulphoxides.

If appropriate, catalysts may be added to accelerate the reaction. Suitable for use as catalysts are, very advantageously, organotin compounds, such as, for example, dibutyltin dilaurate. The reaction is preferably carried out at atmospheric pressure.

In preparation process (H-β) about 1 mol of carbamoyl chloride of the formula (XII) is reacted per mole of starting compound of the formula (I-a) at from −20 to 150° C., preferably from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds of the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes*

*chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Lao-delphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Mono-morium pharaonis, Vespa* spp.

From the order of the Isopoda, for example, *Armadillidium vulgare, Oniscus asellus, Porcellio scaber*.

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp.,

*Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favorable mixing components are, for example, the following compounds:

Fungicides:
Inhibitors of Nucleic Acid Synthesis
  benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid
Inhibitors of Mitosis and Cell Division
  benomyl, carbendazim, diethofencarb, fuberidazole, pencycuron, thiabendazole, thiophanate-methyl, zoxamide
Inhibitors of Respiratory Chain Complex I
  diflumetorim
Inhibitors of Respiratory Chain Complex II
  boscalid, carboxin, fenfuram, flutolanil, furametpyr, mepronil, oxycarboxin, penthiopyrad, thifluzamide
Inhibitors of Respiratory Chain Complex III
  azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin
Decouplers
  dinocap, fluazinam
Inhibitors of ATP Production
  fentin acetate, fentin chloride, fentin hydroxide, silthiofam
Inhibitors of Amino Acid Biosynthesis and Protein Biosynthesis
  andoprim, blasticidin-S, cyprodinil, kasugamycin, kasugamycin hydrochloride hydrate, mepanipyrim, pyrimethanil
Inhibitors of Signal Transduction
  fenpiclonil, fludioxonil, quinoxyfen
Inhibitors of Lipid and Membrane Synthesis
  chlozolinate, iprodione, procymidone, vinclozolin
  ampropylfos, potassium-ampropylfos, edifenphos, iprobenfos (IBP), isoprothiolane, pyrazophos
  tolclofos-methyl, biphenyl
  iodocarb, propamocarb, propamocarb hydrochloride
Inhibitors of Ergosterol Biosynthesis
  fenhexamid,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole,
  aldimorph, dodemorph, dodemorph acetate, fenpropimorph, tridemorph, fenpropidin, spiroxamine,
  naftifine, pyributicarb, terbinafine Inhibitors of Cell Wall Synthesis
  benthiavalicarb, bialaphos, dimethomorph, flumorph, iprovalicarb, polyoxins, polyoxorim, validamycin A
Inhibitors of Melanin Biosynthesis
  capropamid, diclocymet, fenoxanil, phthalid, pyroquilon, tricyclazole
Resistance Inductors
  acibenzolar-S-methyl, probenazole, tiadinil
Multisite
  captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations containing calcium polysulphide, thiram, tolylfluanid, zineb, ziram
Unknown Mechanism
  amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzene-sulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl] pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino] oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxy-phenyl)imino]methyl]thio]methyl]-.alpha.-(methoxymethylene)benzacetate, 4-chloro-alpha-propynyloxy-N-[2-[3-methoxy-4-(2-propynyloxy) phenyl]ethyl]benzacetamide, (2S)—N-[2-[4-[[3-(4-chlorophenyl)-2-propynyl]oxy]-3-methoxyphenyl] ethyl]-3-methyl-2-[(methylsulphon-yl)amino] butanamide, 5-chloro-7-(4-methylpiperidin-1-yl)-6-(2, 4,6-trifluorophenyl)[1,2,4]-triazolo[1,5-a]pyrimidine, 5-chloro-6-(2,4,6-trifluorophenyl)-N-[(1R)-1,2,2-trimethylpropyl]-[1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloro-nicotinamide, 2-butoxy-6-iodo-3-propylbenzopyranon-4-one, N-{(Z)-[(cyclopropylmethoxy)-imino][6-(difluoromethoxy)-2, 3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methyl-acetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
  carbamates,
    for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
  organophosphates,
    for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
  pyrethroids,
    for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cyclprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, teralethrin, tetramethrin (1R isomer), tralomethrin, transfluthrin, ZXI 8901, pyrethrins (pyrethrum)

DDT oxadiazines,
  for example indoxacarb semicarbazones,
  for example metaflumizone (BAS3201)

Acetylcholine Receptor Agonists/Antagonists
  chloronicotinyls,
    for example acetamiprid, clothianidin, dinotefuran, imidacloprid, nitenpyram, nithiazine, thiacloprid, thiamethoxam
  nicotine, bensultap, cartap Acetylcholine Receptor Modulators
  spinosyns,
    for example spinosad GABA-Controlled Chloride Channel Antagonists
  organochlorines,
    for example camphechlor, chlordane, endosulphan, gamma-HCH, HCH, heptachlor, lindane, methoxychlor
  fiprols,
    for example acetoprole, ethiprole, fipronil, pyrafluprole, pyriprole, vaniliprole Chloride Channel Activators
  mectins,
    for example abamectin, emamectin, emamectin-benzoate, ivermectin, lepimectin, milbemycin Juvenile Hormone Mimetics,
    for example diofenolan, epofenonane, fenoxycarb, hydroprene, kinoprene, methoprene, pyriproxifen, triprene Ecdysone Agonists/Disruptors
  diacylhydrazines,
    for example chromafenozide, halofenozide, methoxyfenozide, tebufenozide Chitin Biosynthesis Inhibitors
  benzoylureas,
    for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
  buprofezin
  cyromazine Oxidative Phosphorylation Inhibitors, ATP Disruptors
  diafenthiuron
  organotin compounds,
    for example azocyclotin, cyhexatin, fenbutatin-oxide Oxidative Phosphorylation Decouplers Acting by Interrupting the H-Proton Gradient
  pyrroles,
    for example chlorfenapyr
  dinitrophenols,
    for example binapacyrl, dinobuton, dinocap, DNOC, meptyldinocap Site-I Electron Transport Inhibitors
  METI's,
    for example fenazaquin, fenpyroximate, pyrimidifen, pyridaben, tebufenpyrad, tolfenpyrad hydramethylnon
  dicofol Site-II Electron Transport Inhibitors
  rotenone Site-III Electron Transport Inhibitors
  acequinocyl, fluacrypyrim Microbial Disrupters of the Insect Gut Membrane
*Bacillus thuringiensis* strains
Lipid Synthesis Inhibitors
tetronic acids,
for example spirodiclofen, spiromesifen
tetramic acids,
for example spirotetramat, cis-3-(2,5-dimethylphenyl)-4-hydroxy-8-methoxy-1-azaspiro[4.5]dec-3-en-2-one
carboxamides,
for example flonicamid
octopaminergic agonists,
for example amitraz
Inhibitors of Magnesium-Stimulated ATpase,
propargite
nereistoxin analogs,
for example thiocyclam hydrogen oxalate, thiosultap-sodium
Ryanodine Receptor Agonists,
benzodicarboxamides,
for example flubendiamid
anthranilamides,
for example Rynaxypyr (3-bromo-N-{4-chloro-2-methyl-6-[(methylamino)carbonyl]phenyl}-1-(3-chloropyridin-2-yl)-1H-pyrazole-5-carboxamide)
Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.
Active Compounds with Unknown or Unspecific Mechanisms of Action
fumigants,
for example aluminum phosphide, methyl bromide, sulfuryl fluoride
antifeedants,
for example cryolite, flonicamid, pymetrozine
mite growth inhibitors,
for example clofentezine, etoxazole, hexythiazox
amidoflumet, benclothiaz, benzoximate, bifenazate, bromopropylate, buprofezin, chinomethionat, chlordimeform, chlorbenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particular advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants").

Traits that are also particularly emphasized are the increased defense of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100- to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosus, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate*

*monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga* carnaria, *Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesba-*

*nia, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), benfuresate, bensulfuron (-methyl), bentazone, bencarbazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfurone, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), pyroxsulam, propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrimisulfan, pyrithiobac (-sodium), pyroxasulfone, quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thiencarbazone-methyl, thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron and

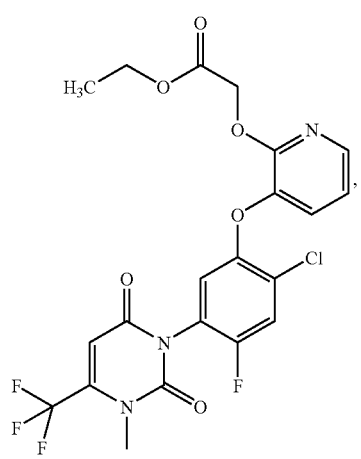

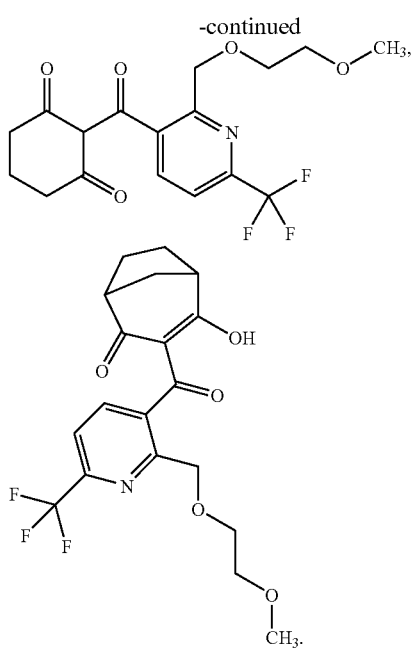

A mixture with other known active compounds, such as fungicides, insecticides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, salts from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by pouring, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), maize, soya beans, potatoes, cotton, oilseed rape, beets, sugar cane and also fruit plants (with the fruits apples, pears, citrus fruit and grapes), with particular emphasis being given to cereals, maize, soya beans, potatoes, cotton and oilseed rape.

In each case, the term "active compound" also includes the active compound combinations mentioned here.

The preparation and the use of the active compounds according to the invention are illustrated by the examples below.

PREPARATION EXAMPLES

Examples I-a-1 and I-a-2

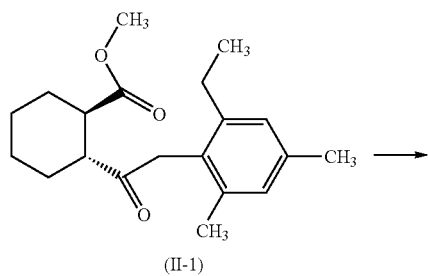

(II-1)

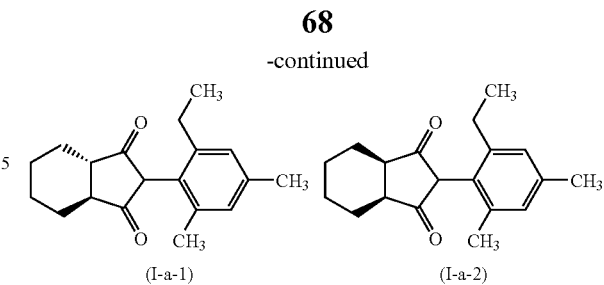

2.50 g (7.9 mmol) of methyl trans-2-[(2-ethyl-4,6-dimethylphenyl)acetyl]cyclohexanecarboxylate and 1.77 g of potassium tert-butoxide (15.8 mmol) are initially charged in 20 ml of anhydrous dimethylformamide, and the mixture is heated at 50° C. for 3 h. After cooling, the mixture is added to ice-water, acidified with 2N hydrochloric acid to pH 2 and extracted with ethyl acetate. The organic phase is washed twice with water, dried (magnesium sulphate) and concentrated using a rotary evaporator. The residue is chromatographed on silica gel using hexane/ethyl acetate (v/v=60:40).

| Fraction A: | trans-isomer I-a-1 |
|---|---|
| Yield: | 0.94 g (42%) |
| M.p.: | 196-197° C. |
| Fraction B: | cis-isomer I-a-2 |
| Yield: | 0.60 g (27%) |
| M.p.: | 220-221° C. |

Analogously to Example (I-1-a-1 and I-a-2) and in accordance with the general statements on the preparation, the following compounds of the formula (I-a) are obtained

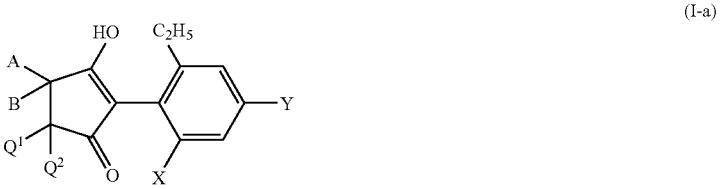

| Ex. No. | X | Y | B | A | $Q^1$ | $Q^2$ | M.p. ° C. | Isomer |
|---|---|---|---|---|---|---|---|---|
| I-a-3 | $CH_3$ | $CH_3$ | | —$(CH_2)_5$— | H | H | 177-178 | — |
| I-a-4 | $CH_3$ | $CH_3$ | H | —$CH_2$—CH=CH—$CH_2$— | | H | 163-164 | cis/trans about 7:3 |

-continued

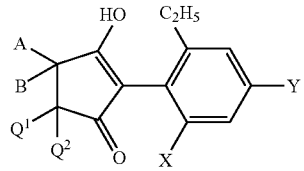

(I-a)

| Ex. No. | X | Y | B | A | Q¹ | Q² | M.p. ° C. | Isomer |
|---|---|---|---|---|---|---|---|---|
| I-a-5 | $CH_3$ | $CH_3$ | $CH_3$ | $CH_3$ | H | H | 230 | — |
| I-a-6 | $CH_3$ | $CH_3$ | —$(CH_2)_4$— | | H | H | *1.05 (t, 3 H), 1.50-2.10 (m, 8 H), 2.05 and 2.15 (in each case s, in each case 3 H), 2.35 (q, 2 H), 2.48 (s, 2 H), 6.90 (s, 2 H) | — |
| I-a-7 | $C_2H_5$ | $CH_3$ | —$(CH_2)_4$— | | H | H | 235 | — |
| I-a-8 | $C_2H_5$ | $CH_3$ | H | —$(CH_2)_4$— | H | H | 195-196 | cis |
| I-a-9 | $C_2H_5$ | $CH_3$ | H | —$(CH_2)_4$— | H | H | 165-166 | trans |
| I-a-10- | $C_2H_5$ | $CH_3$ | H | —$CH_2$—CH=CH—$CH_2$— | H | H | 187-188 | cis |
| I-a-11 | $C_2H_5$ | $CH_3$ | —$(CH_2)_5$— | | H | H | 168-169 | — |
| I-a-12 | $C_2H_5$ | $CH_3$ | H | —$CH_2$—CH—CH—$CH_2$— (O-C(CH_3)_2-O) | H | H | 197-198 | diasteriomer mixture 1 |
| I-a-13 | $C_2H_5$ | $CH_3$ | H | —$CH_2$—CH—CH—$CH_2$— (O-C(CH_3)_2-O) | H | H | 217-218 | diasteriomer mixture 2 |
| I-a-14 | $C_2H_5$ | $CH_3$ | H | —$CH_2$—$CHCH_3$—$(CH_2)_2$— | H | H | 148-149 | mixture |
| I-a-15 | $C_2H_5$ | $C_2H_5$ | H | —$(CH_2)_4$— | H | H | *1.03 (t, 3 H), 1.18-1.25 (m, 6 H), 6.90 (s, 2 H) | cis |
| I-a-16 | $C_2H_5$ | $C_2H_5$ | H | —$(CH_2)_4$— | H | H | *1.05 (t, 3 H), 1.20-1.28 (m, 6 H), 1.92 (m, 2 H), 6.93 (s, 2 H) | trans |
| I-a-17 | $C_2H_5$ | $C_2H_5$ | H | —$CH_2$—$CHCH_3$—$(CH_2)_2$ | H | H | 83-84 | mixture |
| I-a-18 | $CH_3$ | $CH_3$ | H | —$(CH_2)_5$— | H | H | 90-91 | trans |
| I-a-19 | $CH_3$ | $CH_3$ | H | —$(CH_2)_5$— | H | H | 191-192 | cis |
| I-a-20 | $CH_3$ | $CH_3$ | —$(CH_2)_2$—O—$(CH_2)_2$— | | H | H | 203 | — |
| I-a-21 | $CH_3$ | $C_2H_5$ | H | —$(CH_2)_4$— | H | H | 1.80 (m, 2 H) 2.18 (m, 2 H) 2.70 (q, 1 H); 2.83 (q, 1 H) | trans |
| I-a-22 | $CH_3$ | $C_2H_5$ | H | —$(CH_2)_5$— | H | H | 76-77 | trans |
| I-a-23 | $CH_3$ | $C_2H_5$ | H | —$(CH_2)_5$— | H | H | 2.18 + 2.59 (in each case q, in each case 2 H); 2.96 (mc, 2 H) | cis |
| I-a-24 | $C_2H_5$ | $CH_3$ | H | —$(CH_2)_5$— | H | H | 140-141 | trans |
| I-a-25 | $C_2H_5$ | $CH_3$ | H | —$(CH_2)_5$— | H | H | 163-164 | cis |
| I-a-26 | $C_2H_5$ | $CH_3$ | H | —$CH_2$—$CHCH_3$—$CH_2$— | H | H | 71-72 | cis (endo) |
| I-a-27 | $C_2H_5$ | $CH_3$ | H | —$CH_2$—$CHCH_3$—$CH_2$— | H | H | 181-182 | cis (exo) |
| I-a-28 | $C_2H_5$ | $CH_3$ | —$(CH_2)_2$—O—$(CH_2)_2$— | | H | H | 186 | — |
| I-a-29 | $C_2H_5$ | $CH_3$ | H | —$(CH_2)_3$— | H | H | 182-183 | cis |

*¹H-NMR (400 MHz, $CDCl_3$): shift in ppm

Example I-b-1

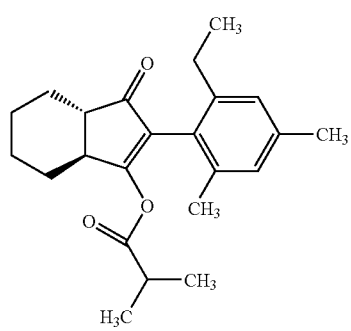

0.13 g (1.2 mmol) of isobutyryl chloride are added to 0.300 g (1.0 mmol) of trans-2-[(2-ethyl-4,6-dimethylphenyl)-3-hydroxyhexahydro-1H-inden-1-one in 5 ml of chloroform and 0.5 ml of triethylamine, and after 1 h of stirring at room temperature the mixture is poured onto ice. The mixture is taken up in chloroform, washed with water and dilute hydrochloric acid and then dried (magnesium sulphate) and concentrated using a rotary evaporator. Subsequent chromatography on silica gel (ethyl acetate/hexane v/v=70:30) gives 0.31 g (83%) of the desired product as a colorless oil.

¹H-NMR (400 MHz, CDCl₃): δ=1.10 (d, 6H), 2.42 (mc, 2H), 2.62 (mc, 2H), 2.98 (mc, 1H) 6.82-6.90 (m, 2H) ppm Example I-b-2

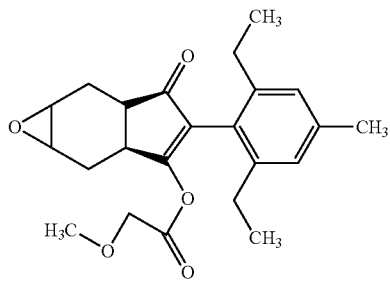

133 mg (0.6 mmol) of m-chloroperbenzoic acid are added to a mixture of 0.2 g (0.54 mmol) of the compound according to Example I-b-43 and 2 ml of 0.5 molar sodium bicarbonate solution in 10 ml of dichloromethane, and the mixture is stirred at room temperature for 2 h. The mixture is then taken up in 30 ml of dichloromethane, washed with 10% strength potassium carbonate solution and water, dried (magnesium sulphate) and concentrated using a rotary evaporator. Chromatography on silica gel (ethyl acetate/hexane v/v=80:20) gives 0.12 g (58%) of the desired product (isomer mixture) as a colorless oil.

¹H-NMR (400 MHz, CDCl₃): δ=2.67 (d, br, 1H), 2.75 (mc, 1H), 3.20 (mc, 1H), 3.27 (mc, 1H), 3.33 (s, 3H), 4.07 (s, 2H) ppm Analogously to Example (I-b-1) and in accordance with the general statements on the preparation, the following compounds of the formula (I-b) are obtained

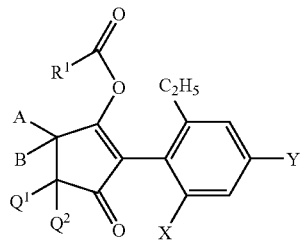

(I-b)

| Ex. No. | X | Y | B | A | Q¹ | Q² | R¹ | ¹H-NMR (300 MHz/ 400 MHz, (CDCl₃): shifts δ in ppm | Isomer |
|---|---|---|---|---|---|---|---|---|---|
| I-b-3 | CH₃ | CH₃ | CH₃ | CH₃ | H | H | CH₃ | 1.23 (s, 6 H), 2.03, 2.10 and 2.29 (in each case s, in each case 3 H) | — |
| I-b-4 | CH₃ | CH₃ | CH₃ | CH₃ | H | H | C₂H₅ | 1.03 (2 × t, in each case 3 H), 2.18 (2 × q, in each case 2 H), 2.90 (s, 2 H) | — |
| I-b-5 | CH₃ | CH₃ | CH₃ | CH₃ | H | H | i-C₃H₇ | 1.04 (d, 6 H), 2.57 (hept, 1 H), 6.85 (s, 2 H) | — |
| I-b-6 | CH₃ | CH₃ | CH₃ | CH₃ | H | H | t-C₄H₉ | 1.05 (s, 9 H), 2.02 and 2.25 (in each case s, in each case 3 H) | — |
| I-b-7 | CH₃ | CH₃ | CH₃ | CH₃ | H | H | H₃C—O—CH₂— | 1.03 (t, 3 H), 3.35 (s, 3 H), 4.02 (s, 2 H) | — |
| I-b-8 | CH₃ | CH₃ | | —(CH₂)₄— | H | H | C₂H₅ | 1.03 and 1.04 (in each case t, in each case 3 H), 2.30-2.42 (m, 4 H), 2.95 (s, 2 H) | — |
| I-b-9 | CH₃ | CH₃ | | —(CH₂)₄— | H | H | i-C₃H₇ | 1.03 (d, 6 H), 1.02 (t, 3 H), 2.58 (hept, 1 H) | — |
| I-b-10 | CH₃ | CH₃ | | —(CH₂)₄— | H | H | t-C₄H₉ | 1.02 (s, 9 H), 2.02 (s, 3 H), 2.25 (s, 3 H) | — |
| I-b-11 | CH₃ | CH₃ | | —(CH₂)₄— | H | H | H₃C—O—CH₂— | 1.63-2.10 (m, 8 H), 3.32 (s, 3 H), 4.02 (s, 2 H) | — |
| I-b-12 | CH₃ | CH₃ | H | —(CH₂)₄— | | H | t-C₄H₉ | 1.03, (s, 9 H), 2.92 (mc, 1 H) | trans |
| I-b-13 | CH₃ | CH₃ | H | —(CH₂)₄— | | H | H₃C—O—CH₂— | 3.00 (mc, 1 H), 3.29 (s, 3 H), 4.02 (s, 2 H) | trans |
| I-b-14 | CH₃ | CH₃ | H | —(CH₂)₄— | | H | t-C₄H₉ | 1.04 (s, 9 H), 6.82 (s, 2 H) | cis |
| I-b-15 | CH₃ | CH₃ | H | —(CH₂)₄— | | H | H₃C—O—CH₂ | 2.70 (mc, 1 H), 3.28 (mc, 1 H), 4.02 (s, 2 H) | cis |
| I-b-16 | CH₃ | CH₃ | H | —(CH₂)₄— | | H | i-C₃H₇ | 1.05 (q, 6 H), 2.62 (hept, 1 H), 2.83 (q, 1 H), 3.42 (q, 1 H), | cis |
| I-b-17 | CH₃ | CH₃ | | —(CH₂)₅— | H | H | t-C₄H₉ | 1.05 (s, 9 H), 2.94 (s, 2 H) | — |
| I-b-18 | CH₃ | CH₃ | | —(CH₂)₅— | H | H | H₃C—O—CH₂ | 1.02 (t, 3 H), 2.94 (s, 2 H), 3.35 (s, 3 H), 4.02 (s, 2 H), | — |

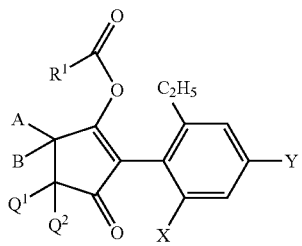

(I-b)

| Ex. No. | X | Y | B | A | $Q^1$ | $Q^2$ | $R^1$ | $^1$H-NMR (300 MHz/ 400 MHz, (CDCl$_3$): shifts δ in ppm | Isomer |
|---|---|---|---|---|---|---|---|---|---|
| I-b-19 | CH$_3$ | CH$_3$ | | —(CH$_2$)$_5$— | H | H | i-C$_3$H$_7$ | 1.02 (d, 6 H), 2.95 (s, 2 H) | — |
| I-b-20 | CH$_3$ | CH$_3$ | H | —CH$_2$—CH=CH—CH$_2$— | H | H | t-C$_4$H$_9$ | 1.05 (s, 9 H), 5.87 and 5.95 (in each case mc, in each case 1 H) | cis/trans about 7:3 |
| I-b-21 | CH$_3$ | CH$_3$ | H | —(CH$_2$)$_4$— | | H | C$_2$H$_5$ | 3.00 (mc, 1 H), 3.79 (mc, 1 H), 4.18 (mc, 2 H) | cis |
| I-b-22 | C$_2$H$_5$ | CH$_3$ | | —(CH$_2$)$_4$— | H | H | H$_3$C—O—CH$_2$— | 1.05 (t, 3 H), 1.60-2.09 (m, 8 H), 2.35 (mc, 4 H) | — |
| I-b-23 | C$_2$H$_5$ | CH$_3$ | H | —(CH$_2$)$_4$— | | H | i-C$_3$H$_7$ | | cis |
| I-b-24 | C$_2$H$_5$ | CH$_3$ | H | —(CH$_2$)$_4$— | | H | t-C$_4$H$_9$ | | cis |
| I-b-25 | C$_2$H$_5$ | CH$_3$ | H | —(CH$_2$)$_4$— | | H | H$_3$C—O—CH$_2$— | 2.88 (q, 1 H), 3.32 (s, 3 H), 3.54 (q, 1 H), 4.03 (s, 2 H) | cis |
| I-b-26 | C$_2$H$_5$ | CH$_3$ | H | —(CH$_2$)$_4$— | | H | t-C$_4$H$_9$ | 1.10 (s, 9 H), 1.95-2.10 (m, 3 H), 3.06 (mc, 1 H), 6.92 (s, 2 H) | trans |
| I-b-27 | C$_2$H$_5$ | CH$_3$ | H | —(CH$_2$)$_4$— | | H | H$_3$C—O—CH$_2$— | 3.02 (mc, 1 H), 3.31 (s, 3 H), 4.05 (s, 2 H), 6.89 (s, 2 H) | trans |
| I-b-28 | C$_2$H$_5$ | CH$_3$ | H | —(CH$_2$)$_4$— | | H | i-C$_3$H$_7$ | 1.18 (d, 6 H), 3.10 (mc, 4 H), 6.98 (s, 2 H) | trans |
| I-b-29 | C$_2$H$_5$ | CH$_3$ | H | —(CH$_2$)$_4$— | | H | H$_5$C$_2$—C(CH$_3$)$_2$— | 0.66 (t, 3 H), 1.97-2.10 (m, 2 H), 3.03 (mc, 1 H) | trans |
| I-b-30 | C$_2$H$_5$ | CH$_3$ | H | —(CH$_2$)$_4$— | | H | i-C$_4$H$_9$ | 0.95 (d, 6 H), 1.10 and 1.18 (in each case t, in each case 3 H), 6.98 (s, 2 H) | trans |
| I-b-31 | C$_2$H$_5$ | CH$_3$ | H | —(CH$_2$)$_4$— | | H | Cl—CH$_2$—C(CH$_3$)$_2$— | 1.09-1.14 (m, 12 H), 3.53 (s, 2 H) | trans |
| I-b-32 | C$_2$H$_5$ | CH$_3$ | | —(CH$_2$)$_5$— | H | H | t-C$_4$H$_9$ | 1.05 (s, 9 H), 2.92 (s, 2 H), 6.93 (s, 2 H) | — |
| I-b-33 | C$_2$H$_5$ | CH$_3$ | | —(CH$_2$)$_5$— | H | H | H$_3$C—O—CH$_2$— | 1.03 (t, 3 H), 3.38 (s, 3 H), 4.05 (s, 2 H) | — |
| I-b-34 | C$_2$H$_5$ | CH$_3$ | | —(CH$_2$)$_5$— | H | H | i-C$_3$H$_7$ | 1.05 (d, 6 H), 2.56 (mc, 1 H), 2.92 (s, 2 H) | — |
| I-b-35 | C$_2$H$_5$ | CH$_3$ | | —(CH$_2$)$_5$— | H | H | H$_5$C$_2$—C(CH$_3$)$_2$— | 0.65 (t, 3 H), 1.02 (s, 6 H) 3.90 (s, 2 H) | — |
| I-b-36 | C$_2$H$_5$ | CH$_3$ | | —(CH$_2$)$_5$— | H | H | i-C$_4$H$_9$ | 0.85 (d, 6 H), 1.98 (sept, 1 H), 2.92 (s, 2 H) | — |
| I-b-37 | C$_2$H$_5$ | CH$_3$ | | —(CH$_2$)$_5$— | H | H | Cl—CH$_2$—C(CH$_3$)$_2$— | 1.17 (s, 6 H), 3.42 (s, 2 H), 6.86 (s, 2 H) | — |
| I-b-38 | C$_2$H$_5$ | CH$_3$ | | —(CH$_2$)$_5$— | H | H | C$_2$H$_5$ | 1.04 (t, 6 H), 1.06 (t, 3 H), 2.95 (s, 2 H) | — |
| I-b-39 | C$_2$H$_5$ | CH$_3$ | | —(CH$_2$)$_5$— | H | H | CH$_3$ | 1.04 (t, 6 H), 2.10 (s, 3 H), 2.28 (s, 3 H) | — |
| I-b-40 | C$_2$H$_5$ | CH$_3$ | H | —CH$_2$—CH=CH—CH$_2$— | | H | t-C$_4$H$_9$ | 1.05 (s, 9 H), 5.70-5.90 (s, 2 H), 6.86 (s, 2 H) | cis/trans about 7:3 |
| I-b-41 | C$_2$H$_5$ | CH$_3$ | H | —CH$_2$—CH—CH—CH$_2$—<br>　　　　　O　　O<br>　　　　　　C<br>　　　　H$_3$C　CH$_3$ | | H | i-C$_3$H$_7$ | 122-123 | diastereomer mixture |
| I-b-42 | C$_2$H$_5$ | C$_2$H$_5$ | H | —(CH$_2$)$_4$— | | H | H$_3$C—O—CH$_2$— | 1.07 and 1.09 (in each case t, in each case 3 H), 1.12 (t, 3 H), 3.30 (s, 3 H), 4.05 (s, 2 H) | trans |
| I-b-43 | C$_2$H$_5$ | CH$_3$ | H | —CH$_2$—CH=CH—CH$_2$— | | H | H$_3$C—O—CH$_2$— | 2.48-2.55 (m, 1 H), 2.70 (mc, 1 H), 4.05 (s, 2 H), 4.75-4.88 (m, 2 H) | mixture |

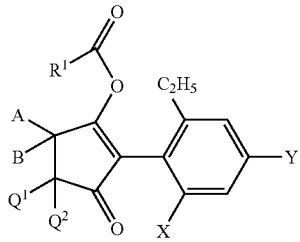

(I-b)

| Ex. No. | X | Y | B | A | Q¹ | Q² | R¹ | ¹H-NMR (300 MHz/ 400 MHz, (CDCl₃): shifts δ in ppm | Isomer |
|---|---|---|---|---|---|---|---|---|---|
| I-b-44 | C₂H₅ | CH₃ | H | —(CH₂)₄— | | H | C₂H₅ | 1.06 and 1.08 (in each case t, in each case 3 H), 3.02 (mc, 1 H), 6.90 (s, 1H) | trans |
| I-b-45 | C₂H₅ | C₂H₅ | H | —(CH₂)₄— | | H | H₃C—O—CH₂— | | cis |
| I-b-46 | C₂H₅ | C₂H₅ | H | —(CH₂)₄— | | H | C₂H₅ | 1.12 (t, 3 H), 2.61 (q, 2 H), 3.03 (mc, 1 H) | trans |
| I-b-47 | C₂H₅ | C₂H₅ | H | —(CH₂)₄— | | H | i-C₃H₇ | 1.05 (d, 6 H), 3.02 (mc, 1 H), 6.90 (s, 2 H) | trans |
| I-b-48 | C₂H₅ | C₂H₅ | —CH₂—CHCH₃—(CH₂)₃— | | H | H | i-C₃H₇ | | mixture |
| I-b-49 | C₂H₅ | C₂H₅ | —CH₂—CHCH₃—(CH₂)₃— | | H | H | H₅C₂—O—CH₂— | | mixture |
| I-b-50 | C₂H₅ | CH₃ | | —(CH₂)₄— | H | H | CH₃ | 1.09 (s, 9 H), 2.10 (s, 3 H), 2.32 (s, 3 H) | |
| I-b-51 | C₂H₅ | CH₃ | | —(CH₂)₄— | H | H | C₂H₅ | 1.05 (3 × t, 9 H), 2.95 (s, 2 H), 6.90 (s, 2 H) | |
| I-b-52 | C₂H₅ | CH₃ | | —(CH₂)₄— | H | H | i-C₃H₇ | 1.03 (d, 6 H), 2.58 (quint, 1 H), 6.95 (s, 2 H) | |
| I-b-53 | C₂H₅ | CH₃ | | —(CH₂)₄— | H | H | t-C₄H₉ | 1.04 (s, 9 H), 6.88 (s, 2 H) | |
| I-b-54 | C₂H₅ | CH₃ | H | —CH₂—CHCH₃—(CH₂)₂— | | H | H₃CO—CH₂— | 0.95 and 0.97 (in each case d, Σ 3 H), 3.32 (s, 3 H), 4.03 (s, 2 H) | isomer mixture |
| I-b-55 | CH₃ | CH₃ | H | —(CH₂)₅— | | H | t-C₄H₉ | 1.03 (s, 9 H) 3.22 (mc, 1 H) | cis |
| I-b-56 | CH₃ | CH₃ | H | —(CH₂)₅— | | H | H₃CO—CH₂— | 3.28 (s, 3 H) 4.02 (s, 2 H) | trans |
| I-b-57 | CH₃ | CH₃ | H | —(CH₂)₅— | | H | i-C₃H₇ | 1.05 (d, 6 H) 3.25 (mc, 1 H) | trans |
| I-b-58 | CH₃ | CH₃ | H | —(CH₂)₅— | | H | H₅C₂—C(CH₃)₂— | 0.55 (t, 3 H) 1.60-1.82 (m, 4 H) | trans |
| I-b-59 | CH₃ | CH₃ | H | —(CH₂)₅— | | H | i-C₄H₉ | 0.78 (d, 6 H) 2.55 (mc, 1 H) | trans |
| I-b-60 | CH₃ | CH₃ | H | —(CH₂)₅— | | H | Cl—CH₂—C(CH₃)₂— | 1.02 (s, 6 H) 3.42 (d, 1 H) 3.44 (d, 1 H) | trans |
| I-b-61 | CH₃ | CH₃ | | —(CH₂)₂—O—(CH₂)₂— | H | H | t-C₄H₉ | 1.08 (s, 9 H) 3.58 (mc, 2 H) 4.03 (mc, 2 H) | — |
| I-b-62 | CH₃ | CH₃ | | —(CH₂)₂—O—(CH₂)₂— | H | H | H₃CO—CH₂— | 3.35 (s, 2 H) 4.05 (s, 3 H) | — |
| I-b-63 | CH₃ | CH₃ | | —(CH₂)₂—O—(CH₂)₂— | H | H | i-C₃H₇ | 1.03 (d, 6 H) 2.58 (hept., 1 H) 3.00 (s, 3 H) | — |
| I-b-64 | CH₃ | CH₃ | | —(CH₂)₂—O—(CH₂)₂— | H | H | H₅C₂—C(CH₃)₂— | 0.62 (t, 3 H) 1.04 (s, 6 H) | — |
| I-b-65 | CH₃ | CH₃ | | —(CH₂)₂—O—(CH₂)₂— | H | H | i-C₄—H₉ | 0.84 (d, 6 H) 1.05 (t, 3 H) 1.99 (hept., 1 H) | — |
| I-b-66 | CH₃ | CH₃ | | —(CH₂)₂—O—(CH₂)₂— | H | H | ClCH₂—C(CH₃)₂— | 1.18 (s, 6 H) 3.42 (s, 2H) | — |
| I-b-67 | CH₃ | CH₃ | | —(CH₂)₂—O—(CH₂)₂— | H | H | C₂H₅ | 1.04 (t, 3 H) 2.38 (q, 2 H) 3.01 (s, 2 H) | — |
| I-b-68 | CH₃ | CH₃ | | —(CH₂)₂—O—(CH₂)₂— | H | H | CH₃ | 2.02 (s, 3 H) 2.12 (s, 3 H) 2.29 (s, 3 H) | — |
| I-b-69 | CH₃ | C₂H₅ | H | —(CH₂)₄— | | H | H₃CO—CH₂— | 3.00 (1 H) 3.31 (s, 3 H) 4.03 (s, 2 H) | trans |
| I-b-70 | CH₃ | C₂H₅ | H | —(CH₂)₅— | | H | t-C₄H₉ | 1.04 (s, 9 H) 3.22 (mc, 1 H) | trans |
| I-b-71 | CH₃ | C₂H₅ | H | —(CH₂)₅— | | H | H₃CO—CH₂— | 3.28 (s, 3 H) 4.02 (s, 2 H) | trans |

-continued

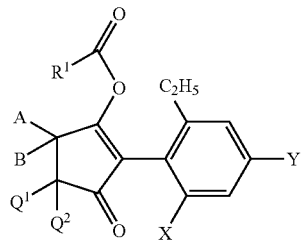
(I-b)

| Ex. No. | X | Y | B | A | Q¹ | Q² | R¹ | $^1$H-NMR (300 MHz/ 400 MHz, (CDCl$_3$): shifts δ in ppm | Isomer |
|---|---|---|---|---|---|---|---|---|---|
| I-b-72 | CH$_3$ | C$_2$H$_5$ | H | —(CH$_2$)$_5$— |  | H | i-C$_3$H$_7$ | 1.09 (d, 6 H) 3.22 (mc, 1 H) 6.85 (s, 2 H) | trans |
| I-b-73 | C$_2$H$_5$ | CH$_3$ | H | —(CH$_2$)$_5$— |  | H | H$_3$CO—CH$_2$— | 3.28 (s, 3 H) 3.62 (mc, 1 H) | cis |
| I-b-74 | C$_2$H$_5$ | CH$_3$ | H | —(CH$_2$)$_5$— |  | H | H$_3$CO—CH$_2$— | 1.05 (s, 9 H) 2.28 (s, 3 H) 4.01 (s, 2 H) | trans |
| I-b-75 | C$_2$H$_5$ | CH$_3$ | H | —(CH$_2$)$_5$— |  | H | t-C$_4$H$_9$ | 1.05 (s, 9 H) 2.28 (s, 3 H) 1.98 (mc, 1 H) | trans |
| I-b-76 | C$_2$H$_5$ | CH$_3$ | H | —(CH$_2$)$_5$— |  | H | i-C$_3$H$_7$ | 1.02 (d, 6 H) 2.56 (hept., 1 H) 3.32 (mc, 1 H) | trans |
| I-b-77 | C$_2$H$_5$ | CH$_3$ | H | —(CH$_2$)$_5$— |  | H | CH$_3$ | 2.09 (s, 3 H) 2.30 (s, 3 H) 6.90 (s, 2 H) | trans |
| I-b-78 | C$_2$H$_5$ | CH$_3$ | H | —(CH$_2$)$_5$— |  | H | t-C$_4$H$_9$ | 1.05 (s, 9 H) 3.60 (mc, 1 H) | cis |
| I-b-79 | C$_2$H$_5$ | CH$_3$ | H | —(CH$_2$)$_5$— |  | H | i-C$_3$H$_7$ | 1.02 (d, 6 H) 3.58 (hept., 1 H) | cis |
| I-b-80 | C$_2$H$_5$ | CH$_3$ | H | —CH$_2$—CHCH$_3$—CH$_2$— |  | H | H$_3$CO—CH$_2$— | 1.04 (mc, 9 H) 4.02 (s, 2 H) | cis endo/exo |
| I-b-81 | C$_2$H$_5$ | CH$_3$ | H | —CH$_2$—CHCH$_3$—CH$_2$— |  | H | C$_2$H$_5$ | 1.00-1.15 (m, 9 H) 6.89 (s, 2 H) | cis endo/exo |
| I-b-82 | C$_2$H$_5$ | CH$_3$ | H | —CH$_2$—CHCH$_3$—CH$_2$— |  | H | CH$_3$ | 2.10 (s, 3 H) 2.25 (s, 3 H) | cis endo/exo |
| I-b-83 | C$_2$H$_5$ | CH$_3$ | H | —CH$_2$—CHCH$_3$—CH$_2$— |  | H | t-C$_4$H$_9$ | 1.02 (s, 9 H) 6.95 (s, 2 H) | cis endo/exo |
| I-b-84 | C$_2$H$_5$ | CH$_3$ |  | —(CH$_2$)$_2$—O—(CH$_2$)$_2$— | H | H | t-C$_4$H$_9$ | 1.03 (s, 9 H) 2.30 (s, 3 H) 3.00 (s, 3 H) | — |
| I-b-85 | C$_2$H$_5$ | CH$_3$ |  | —(CH$_2$)$_2$—O—(CH$_2$)$_2$— | H | H | H$_3$CO—CH$_2$— | 3.35 (s, 2 H) 4.04 (s, 3 H) | — |
| I-b-86 | C$_2$H$_5$ | CH$_3$ |  | —(CH$_2$)$_2$—O—(CH$_2$)$_2$— | H | H | i-C$_3$H$_7$ | 1.05 (d, 6 H) 2.60 (hept, 1 H) 3.03 (s, 2 H) | — |
| I-b-87 | C$_2$H$_5$ | CH$_3$ |  | —(CH$_2$)$_2$—O—(CH$_2$)$_2$— | H | H | H$_5$C$_2$—C(CH$_3$)$_2$— | 1.03 (s, 6 H) 0.62 (t, 3 H) 3.00 (s, 2 H) | — |
| I-b-88 | C$_2$H$_5$ | CH$_3$ |  | —(CH$_2$)$_2$—O—(CH$_2$)$_2$— | H | H | i-C$_4$H$_9$ | 0.85 (d, 6 H) 1.03 (t, 6 H) 1.98 (hept, 1 H) | — |
| I-b-89 | C$_2$H$_5$ | CH$_3$ |  | —(CH$_2$)$_2$—O—(CH$_2$)$_2$— | H | H | ClCH$_2$—C(CH$_3$)$_2$— | 1.15 (s, 6 H) 3.42 (s, 2 H) | — |
| I-b-90 | C$_2$H$_5$ | CH$_3$ |  | —(CH$_2$)$_2$—O—(CH$_2$)$_2$— | H | H | C$_2$H$_5$ | 1.04 (t, 3 H) 2.39 (q, 2 H) 3.04 (s, 2 H) | — |
| I-b-91 | C$_2$H$_5$ | CH$_3$ |  | —(CH$_2$)$_2$—O—(CH$_2$)$_2$— | H | H | CH$_3$ | 1.03 (t, 6 H) 2.11 (s, 3 H) 2.32 (s, 3 H) | — |
| I-b-92 | C$_2$H$_5$ | CH$_3$ | H | —CH$_2$—CHCH$_3$—CH$_2$— |  | H | i-C$_3$H$_7$ | 1.04 (d, 6 H) 2.57 (hept, 1 H) 3.12 (dt, 1 H) 3.88 (dt, 1 H) | exo |
| I-b-93 | C$_2$H$_5$ | CH$_3$ | H | —CH$_2$—CHCH$_3$—CH$_2$— |  | H | i-C$_3$H$_7$ | 1.07 (d, 6 H) 2.57 (hept, 1 H) 3.22 (mc, 1 H) 3.95 (dt, 1 H) | endo |
| I-b-94 | C$_2$H$_5$ | CH$_3$ | H | —CH$_2$—CHCH$_3$—CH$_2$— |  | H | i-C$_3$H$_7$ | 2.58 (hept, 1 H) 3.10-3.23 (mc, 1 H) | cis endo/exo |

Example I-c-1

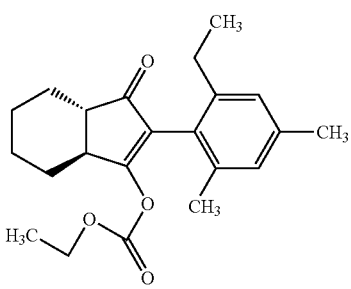

75 mg g (0.7 mmol) of ethyl chloroformate are added to 0.200 g (0.7 mmol) of trans-2-[(2-ethyl-4,6-dimethylphenyl)-3-hydroxyhexahydro-1H-inden-1-one (Ex. I-a-1) in 5 ml of chloroform and 0.5 ml of triethylamine, and the mixture is stirred at room temperature for 1 h. The mixture is diluted with about 30 ml of chloroform, transferred into a separating funnel und washed successively with water, 2N hydrochloric acid and again with water, dried (magnesium sulphate) and, after distillative removal of the solvent, chromatographed on silica gel (ethyl acetate/hexane v:v=90:10). This gives 0.21 g (84%) of the title compound as a colorless oil.

$^1$H-NMR (400 MHz, CDCl$_3$): δ=1.08 (t, 3H), 1.13 (t, 3H), 2.62 (mc, 1H), 3.01 (mc, 1H), 4.18 (q, 2H), 6.90 (mc, 2H) ppm.

Analogously to Example (I-c-1) and in accordance with the general statements on the preparation, the following compounds of the formula (I-c) are obtained

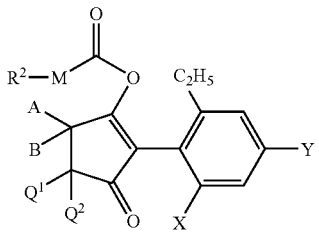

(I-c)

| Ex. No. | X | Y | B | A | Q$^1$ | Q$^2$ | M | R$^2$ | $^1$H-NMR (300 MHz/ 400 MHz, CDCl$_3$): shifts δ in ppm | Isomer |
|---|---|---|---|---|---|---|---|---|---|---|
| I-c-2 | CH$_3$ | CH$_3$ | CH$_3$ | CH$_3$ | H | H | O | C$_2$H$_5$ | 1.05 (t, 3 H), 1.14 (t, 3 H), 4.19 (q, 2 H) | — |
| I-c-3 | CH$_3$ | CH$_3$ | —(CH$_2$)$_4$— | | H | H | O | C$_2$H$_5$ | 1.05 and 1.22 (in each case t, in each case 3 H), 4.18 (q, 2 H) | — |
| I-c-4 | CH$_3$ | CH$_3$ | H | —(CH$_2$)$_4$— | H | H | O | C$_2$H$_5$ | 3.10 (mc, 1-H) 4.22 (mc, 1 H) | cis |
| I-c-5 | CH$_3$ | CH$_3$ | —(CH$_2$)$_5$— | | H | H | O | C$_2$H$_5$ | 1.03 and 1.15 (in each case t, in each case 3 H), 4.20 (q, 2 H) | — |
| I-c-6 | CH$_3$ | CH$_3$ | H | —CH$_2$—CH=CH—CH$_2$— | H | H | O | C$_2$H$_5$ | 3.00 (mc, 1 H) 4.18 (mc, 2 H) | cis/trans 7:3 |
| I-c-7 | C$_2$H$_5$ | CH$_3$ | —(CH$_2$)$_4$— | | H | H | O | C$_2$H$_5$ | 1.25 (t, 3 H), 1.63-2.09 (m, 8 H), 3.00 (s, 2 H), 4.19 (q, 2 H) | — |
| I-c-8 | C$_2$H$_5$ | CH$_3$ | H | —(CH$_2$)$_4$— | H | H | O | C$_2$H$_5$ | 1.36 (t, 3 H), 3.12 (mc, 1 H), 4.25 (q, 2 H), 6.98 (s, br, 2 H) | cis |
| I-c-9 | C$_2$H$_5$ | CH$_3$ | H | —(CH$_2$)$_4$— | H | H | O | C$_2$H$_5$ | 1.26 (t, 3 H), 2.33 (s, 3 H), 3.03 (mc, 1 H) 4.18 (q, 2 H) | trans |
| I-c-10 | C$_2$H$_5$ | CH$_3$ | H | —(CH$_2$)$_4$— | H | H | O | CH$_3$ | 2.30 (s, 3 H), 3.02 (s, 1 H), 3.78 (s, 3 H) | trans |
| I-c-11 | C$_2$H$_5$ | CH$_3$ | H | —CH$_2$—CH=CH—CH$_2$— | H | H | O | C$_2$H$_5$ | 1.21 (t, 3 H), 4.15 (mc, 2 H), 6.85 and 6.95 (in each case mc, in each case 1 H) | cis/trans 7:3 |
| I-c-12 | C$_2$H$_5$ | CH$_3$ | —(CH$_2$)$_5$— | | H | H | O | C$_2$H$_5$ | 1.29 (t, 3 H), 2.99 (s, 2 H), 4.22 (q, 2 H) | — |
| I-c-13 | C$_2$H$_5$ | CH$_3$ | —(CH$_2$)$_5$— | | H | H | O | CH$_3$ | 1.05 (t, 3 H), 2.11 (s, 3 H), 2.32 (s, 3 H), 2.95 (s, 2 H) | — |
| I-c-14 | C$_2$H$_5$ | CH$_3$ | H | —(CH$_2$)$_4$— | H | H | O | CH$_3$ | 2.85 (q, 1 H), 3.54 (q, 1 H), 3.74 (s, 3 H) | cis |
| I-c-15 | C$_2$H$_5$ | C$_2$H$_5$ | H | —(CH$_2$)$_4$— | H | H | O | C$_2$H$_5$ | oil | cis |
| I-c-16 | C$_2$H$_5$ | CH$_3$ | H | —CH$_2$—CH—CH—CH$_2$— with O—C(CH$_3$)$_2$—O bridge 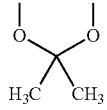 | H | H | O | C$_2$H$_5$ | 112 | diastereomer mixture |

-continued

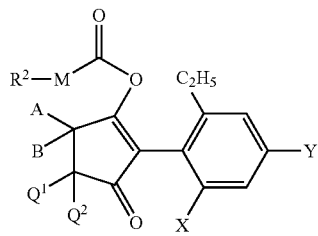

(I-c)

| Ex. No. | X | Y | B | A | $Q^1$ | $Q^2$ | M | $R^2$ | $^1$H-NMR (300 MHz/ 400 MHz, CDCl$_3$): shifts δ in ppm | Isomer |
|---|---|---|---|---|---|---|---|---|---|---|
| I-c-17 | C$_2$H$_5$ | CH$_3$ | H | —CH$_2$—CHCH$_3$—(CH$_2$)$_2$— | | H | O | C$_2$H$_5$ | oil | mixture |
| I-c-18 | C$_2$H$_5$ | C$_2$H$_5$ | H | —(CH$_2$)$_4$— | | H | O | C$_2$H$_5$ | 1.03 and 1.06 (in each case t, in each case 3 H), 1.12 and 1.14 (in each case t, in each case 3 H), 2.61 (q, 2 H), 4.19 (q, 2 H) | trans |
| I-c-19 | CH$_3$ | CH$_3$ | H | —(CH$_2$)$_5$— | | H | O | C$_2$H$_5$ | 1.07 (t, 3 H) 1.22 (t, 3 H) 4.15 (mc, 2 H) | trans |
| I-c-20 | CH$_3$ | CH$_3$ | —(CH$_2$)$_2$—O—(CH$_2$)$_2$— | | H | H | O | C$_2$H$_5$ | 1.03 (t, 3 H) 1.25 (t, 3 H) 4.22 (q, 2 H) | — |
| I-c-21 | CH$_3$ | CH$_3$ | —(CH$_2$)$_2$—O—(CH$_2$)$_2$— | | H | H | O | CH$_3$ | 2.02 (s, 3 H) 3.04 (s, 2 H) 3.79 (s, 3 H) | — |
| I-c-22 | CH$_3$ | C$_2$H$_5$ | H | —(CH$_2$)$_5$— | | H | O | C$_2$H$_5$ | 1.07 (mc, 3 H) 1.18-1.23 (m, 6 H) 3.28 (mc, 1 H) 4.19 (mc, 2 H) | trans |
| I-c-23 | C$_2$H$_5$ | CH$_3$ | H | —(CH$_2$)$_5$— | | H | O | C$_2$H$_5$ | 2.58 (mc, 1 H) 3.38 (mc, 1 H) 4.19 (mc, 1 H) | trans |
| I-c-24 | C$_2$H$_5$ | CH$_3$ | H | —(CH$_2$)$_5$— | | H | O | CH$_3$ | 2.58 (mc, 1 H) 3.37 (mc, 1 H) 3.75 (s, 3 H) | trans |
| I-c-25 | C$_2$H$_5$ | CH$_3$ | H | —(CH$_2$)$_5$— | | H | O | C$_2$H$_5$ | 2.93 (mc, 1 H) 3.63 (mc, 1 H) 4.18 (mc, 2 H) | cis |
| I-c-26 | C$_2$H$_5$ | CH$_3$ | H | —CH$_2$—CHCH$_3$—CH$_2$— | | H | O | C$_2$H$_5$ | 1.25 (2 × t, Σ 3 H) 3.10-3.26 (mc, 1 H) 4.17 (mc, 2 H) | cis endo/exo |
| I-c-27 | C$_2$H$_5$ | CH$_3$ | —(CH$_2$)$_2$—O—(CH$_2$)$_2$— | | H | H | O | C$_2$H$_5$ | 1.05 (t, 6 H) 1.28 (t, 3 H) 4.21 (q, 2 H) | — |
| I-c-28 | C$_2$H$_5$ | CH$_3$ | —(CH$_2$)$_2$—O—(CH$_2$)$_2$— | | H | H | O | CH$_3$ | 1.05 (t, 6 H) 3.10 (s, 3 H) 3.80 (s, 3 H) | — |
| I-c-29 | C$_2$H$_5$ | CH$_3$ | H | —CH$_2$—CHCH$_3$—CH$_2$— | | H | O | C$_2$H$_5$ | 1.23 (t, 3 H) 3.13 (dt, 1 H) 3.95 (dt, 1 H) 4.18 (q, 1 H) | exo |
| I-c-30 | C$_2$H$_5$ | CH$_3$ | H | —CH$_2$—CHCH$_3$—CH$_2$— | | H | O | C$_2$H$_5$ | 1.21 (t, 3 H) 3.22 (mc, 1 H) 3.98 (mc, 1 H) 4.19 (mc, 2 H) | endo |

Example I-e-1

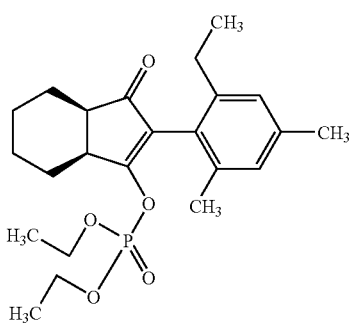

cf. Example 1-c-1

In an analogous manner (cf. Ex. I-c-1), 0.30 g (1 mmol) of cis-2-(ethyl-4,6-dimethylphenyl)-3-hydroxyhexahydro-1H-inden-1-one and 0.18 g (1 mmol) of diethyl phosphoryl chloride give, after column chromatography (ethyl acetate/hexane v:v=85:15), 0.29 g (65%) of the title compound as a colorless oil.

$^1$H-NMR (300 MHz, CDCl$_3$): δ=1.08-1.20 (m, 9H), mc=1.95 (mc, 2H), 2.10 and 2.25 (in each case s, in each case 3H), 2.82 (mc, 1H), 3.65-3.92 (m, 4H), 6.85 (mc, 2H) ppm.

Analogously to Example (I-e-1) and in accordance with the general statements on the preparation, the following compounds of the formula (I-e) are obtained (I-e)

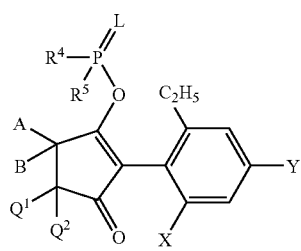

| Ex. No. | X | Y | B | A | Q$^1$ | Q$^2$ | L | R$^4$ | R$^5$ | $^1$H-NMR (300 MHz/ 400 MHz, CDCl$_3$): shifts δ in ppm | Isomer |
|---|---|---|---|---|---|---|---|---|---|---|---|
| I-e-2 | CH$_3$ | CH$_3$ | H | —(CH$_2$)$_4$— | | H | O | OCH$_3$ | OCH$_3$ | 2.83 (mc, 1 H), 3.35 (mc, 1 H), 3.42 (d, 3 H), 3.62 (d, 3 H) | cis |
| I-e-3 | CH$_3$ | CH$_3$ | H | —(CH$_2$)$_4$— | | H | O | OCH$_3$ | OCH$_3$ | 1.05 (t, 3 H), 2.83 (mc, 1 H), 6.89 (mc, 2 H) | trans |
| I-e-4 | CH$_3$ | CH$_3$ | H | —(CH$_2$)$_4$— | | H | O | OC$_2$H$_5$ | OC$_2$H$_5$ | 1.09-1.20 (3 × t, Σ 9 H), 2.83 (mc, 1 H), 3.65-3.90 (m, 4 H) | trans |
| I-e-5 | CH$_3$ | CH$_3$ | H | —(CH$_2$)$_4$— | | H | O | OC$_4$H$_9$ | OC$_4$H$_9$ | 2.82 (mc, 1 H), 3.60-3.84 (m, 4 H) | trans |
| I-e-6 | CH$_3$ | CH$_3$ | H | —(CH$_2$)$_4$— | | H | O | OC$_4$H$_9$ | OC$_4$H$_9$ | 0.82 (t, 3 H), 0.89 (t, 3 H), 1.06 (t, 3 H), 3.72 and 3.90 (in each case mc, in each case 2 H) | cis |
| I-e-7 | C$_2$H$_5$ | CH$_3$ | H | —(CH$_2$)$_4$— | | H | O | OCH$_3$ | OCH$_3$ | | trans |
| I-e-8 | C$_2$H$_5$ | CH$_3$ | H | —(CH$_2$)$_4$— | | H | O | OC$_4$H$_9$ | OC$_4$H$_9$ | 0.80-0.90 (2 × t, Σ 6 H) 1.09-1.14 (2 × t, Σ 6 H) 3.62-3.80 (m, 4 H) | trans |
| I-e-9 | C$_2$H$_5$ | CH$_3$ | H | —(CH$_2$)$_4$— | | H | O | O-i-C$_4$H$_9$ | O-i-C$_4$H$_9$ | 0.79 and 0.83 (in each case d, in each case 6 H) 2.40 (mc, 4 H) 3.35-3.54 (m, 4 H) | trans |
| I-e-10 | C$_2$H$_5$ | CH$_3$ | H | —(CH$_2$)$_4$— | | H | O | OC$_2$H$_5$ | OC$_2$H$_5$ | 2.19 (mc, 4 H), 3.82 (mc, 1 H), 3.76-3.90 (m, 4 H) | trans |
| I-e-11 | C$_2$H$_5$ | CH$_3$ | H | —(CH$_2$)$_4$— | | H | O | Cl—(CH$_2$)$_2$O— | Cl—(CH$_2$)$_2$O— | 1.10 (t, 6 H), 3.42 (mc, 4 H) 3.80-3.98 (m, 4 H) | trans |
| I-e-12 | C$_2$H$_5$ | CH$_3$ | H | —(CH$_2$)$_4$— | | H | O | OCH$_3$ | OCH$_3$ | 2.82 (mc, 1 H), 3.42 and 3.44 (in each case d, in each case 3 H) | cis |
| I-e-13 | CH$_3$ | CH$_3$ | H | —(CH$_2$)$_4$— | | H | O | OC$_2$H$_5$ | OC$_2$H$_5$ | 2.85 (mc, 1 H), 3.39 (mc, 1 H), 3.79 (dt, 2 H) | cis |
| I-e-14 | C$_2$H$_5$ | CH$_3$ | H | —(CH$_2$)$_4$— | | H | O | OC$_4$H$_9$ | OC$_4$H$_9$ | | cis |
| I-e-15 | C$_2$H$_5$ | CH$_3$ | H | —(CH$_2$)$_4$— | | H | O | O-i-C$_4$H$_9$ | O-i-C$_4$H$_9$ | 0.75 and 0.88 (in each case d, in each case 6 H), 3.42 and 3.70 (in each case mc, in each case 2 H) | |
| I-e-16 | C$_2$H$_5$ | CH$_3$ | H | —(CH$_2$)$_4$— | | H | O | Cl—(CH$_2$)$_2$O— | Cl—(CH$_2$)$_2$O— | 2.84 (mc, 1 H), 3.35 (mc, 1 H), 3.39 (t, 2 H), 3.57 (t, 2 H) | cis |
| I-e-17 | C$_2$H$_5$ | CH$_3$ | H | —(CH$_2$)$_5$— | | H | O | OCH$_3$ | OCH$_3$ | 3.12 (mc, 1 H), 3.33 (d, 3 H), 3.58 (d, 3 H) | trans |

(I-e)

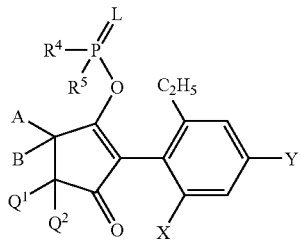

| Ex. No. | X | Y | B | A | $Q^1$ | $Q^2$ | L | $R^4$ | $R^5$ | $^1$H-NMR (300 MHz/ 400 MHz, CDCl$_3$): shifts δ in ppm | Isomer |
|---|---|---|---|---|---|---|---|---|---|---|---|
| I-e-18 | $C_2H_5$ | $CH_3$ | H | $CH_2$—$CHCH_3$—$CH_2$— | H | O | $OCH_3$ | $OCH_3$ | 3.48 and 3.53 (2 × d, Σ 3 H), 3.67 and 3.71 (2 × d, Σ 3 H), 6.89 (mc, 2 H) | cis endo/exo |

Example II-1

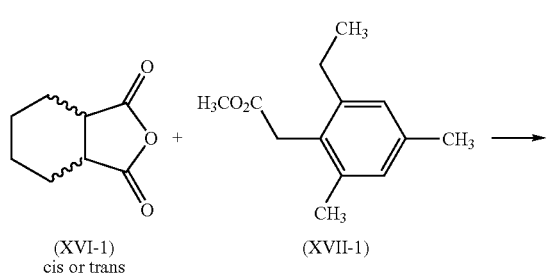

(XVI-1)
cis or trans (XVII-1)

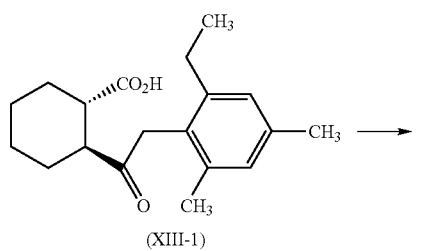

(XIII-1)

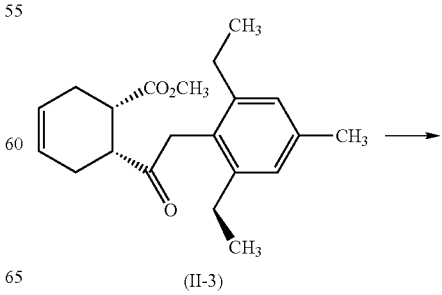

trans (II-1)

At −30° C., 9.0 g (43.6 mmol) of methyl 2-ethyl-4,6-dimethylphenylacetate are slowly added dropwise to a solution of lithium 2,2,6,6-tetramethylpiperidide, prepared from 15.4 g (109 mmol) of 2,2,6,6-tetramethylpiperidine in 80 ml THF and 43.7 ml (109 mmol) of a 2.5 molar solution of n-butyllithium in hexane, and the mixture is stirred at room temperature for another 30 min. At −20° C., 6.7 g (43.6 mmol) of cyclohexane-1,2-dicarboxylic anhydride, dissolved in 20 ml of THF, are then added, and the mixture is stirred at room temperature for 12 h. Addition of 50 ml of sat. ammonium chloride solution, extraction with ethyl acetate, washing of the extract with water, drying (magnesium sulphate) and concentration using a rotary evaporator give about 10 g of a solid, to which 12 mg of potassium hydroxide in 100 ml of water are added, and the mixture is heated under reflux for 24 h. The mixture is then acidified with 2N hydrochloric acid to pH 2, and the solid is filtered off with suction. This gives 5.3 g (40%) of 2-[2-ethyl-4,6-dimethyl-phenyl)acetyl]cyclohexanecarboxylic acid as a yellowish solid which can be used without further purification for the next reaction step.

5.0 g (16.5 mmol) of this intermediate in 30 ml of acetone together with 2 g of potassium carbonate and 5 g (35 mmol) of iodomethane are boiled under reflux for 4 h, then taken up in ethyl acetate, shaken with water and dried (magnesium sulphate), and the solvent is distilled off. Chromatography on silica gel with ethyl acetate/hexane (v/v=80:20) gives 2.69 g (52%) of the desired methyl 2-[2-ethyl-2,6-dimethylphenyl)acetyl]cyclohexanecarboxylate in the form of colorless crystals.

$^1$H-NMR (400 MHz, CDCl$_3$): δ=1.17 (t, 3H), 2.17 and 2.26 (in each case t, in each case 3H), 2.48 (q, 2H), 2.72 (mc, 1H) 2.88, (mc, 1H), 3.60 (s, 3H), 3.93 (AB system, 2H), 6.94 and 6.97 (in each case s, in each case 1H) ppm.

The compounds of the formula (II) required for process (A) are obtained analogously to Example (II-1) and in accordance with the general statements.

Compounds of the formula (II) are furthermore obtained by the process described below:

(II-3)

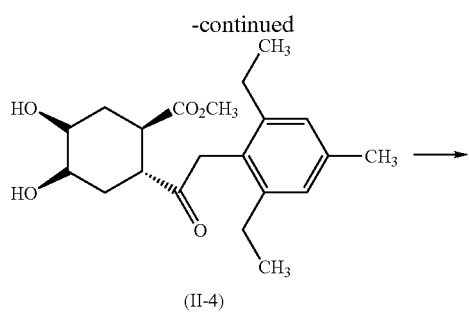

(II-4)

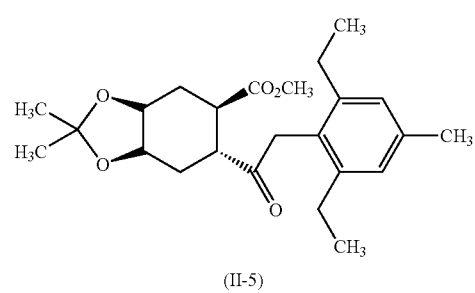

(II-5)

At room temperature, 1.5 ml of osmium tetroxide solution (2.5 M solution in tert-butanol), 860 mg of N-methylmorpholine oxide (NMO) and 2.0 g (6.0 mmol) of methyl 6-[2,6-diethyl-4-methylphenyl)acetyl]cyclohex-3-enecarboxylate in 15 ml of acetone are stirred for 12 h. 700 mg of sodium dithionite are added, and the mixture is stirred at room temperature for 30 min and then extracted with ethyl acetate. After drying (magnesium sulphate) and concentration using a rotary evaporator, about 1.8 g of a viscous oil remain, which are taken up in 5 ml of dimethoxypropane and, after addition of 20 g of p-toluenesulphonic acid, stirred at room temperature for 8 h. The reaction mixture is then washed with 10% strength aqueous potassium carbonate solution, dried (magnesium sulphate) and concentrated using a rotary evaporator. This gives 1.05 g of the compound (II-5).

$^1$H-NMR (300 MHz, CDCl$_3$): δ=1.45 (s, 3H), 1.52 (s, 3H), 2.88 (mc, 1H), 3.20 (mc, 1H), 3.39 (mc, 1H) ppm.

Analogously to Example (II-1) and in accordance with the general statements on the preparation, the following compounds of the formula (II) are obtained:

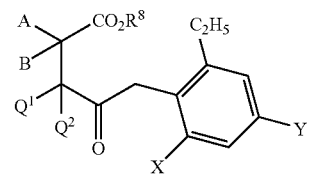

(II)

| Ex. No. | X | Y | B | A | Q$^1$ | Q$^2$ | R$^8$ | M.p. ° C./$^1$H-NMR (300 MHz/400 MHz) shifts δ in ppm | Isomer |
|---|---|---|---|---|---|---|---|---|---|
| II-6 | CH$_3$ | CH$_3$ | | —(CH$_2$)$_4$— | H | H | CH$_3$ | 2.80 (s, 2 H) 3.61 (s, 3 H) 3.63 and 3.72 (in each case d, in each case 1 H) | — |
| II-7 | CH$_3$ | CH$_3$ | | —(CH$_2$)$_5$— | H | H | CH$_3$ | 2.78 (s, 2 H) 3.63 (s, 3 H) 3.68 (s, 2 H) | — |
| II-8 | CH$_3$ | CH$_3$ | H | —CH$_2$—CH=CH—CH$_2$— | H | CH$_3$ | | 80 | cis |
| II-9 | CH$_3$ | CH$_3$ | H | —(CH$_2$)$_5$— | H | CH$_3$ | | 61-62 | trans |
| II-10 | C$_2$H$_5$ | CH$_3$ | H | —(CH$_2$)$_4$— | H | CH$_3$ | | 73-74 | cis |
| II-11 | C$_2$H$_5$ | CH$_3$ | H | —(CH$_2$)$_4$— | H | CH$_3$ | | 69-70 | trans |
| II-12 | C$_2$H$_5$ | CH$_3$ | H | —(CH$_2$)$_5$— | H | CH$_3$ | | 43-44 | trans |
| II-13 | C$_2$H$_5$ | CH$_3$ | H | —CH$_2$—CH=CH—CH$_2$— | H | CH$_3$ | | 92-93 | trans |
| II-14 | C$_2$H$_5$ | CH$_3$ | | —(CH$_2$)$_2$—O—(CH$_2$)$_2$— | H | H | CH$_3$ | 2.30 (s, 3 H) 2.45 (q, 4 H) 2.80 (s, 2 H) 3.65 (s, 3 H) 3.72 (s, 2 H) | — |

Analogously to Example (XII-1) and in accordance with the general statements on the preparation, the following compound of the formula (XIII) is obtained:

(XIII)

[Structure: benzene ring with C₂H₅ at ortho position and Y at para position, connected via CH₂-C(=O)- to a carbon bearing A, B, Q¹, Q² and CO₂H group, labeled with X on the carbonyl]

| Ex. No. | X | Y | B | A | Q¹ | Q² | M.p. °C. | Isomer |
|---|---|---|---|---|---|---|---|---|
| XIII-2 | C₂H₅ | CH₃ | H | —(CH₂)₄— | | H | 200 | trans |
| XIII-3 | C₂H₅ | CH₃ | —(CH₂)₂—O—(CH₂)₂ | | H | H | 115 | — |

Test Description

Example A

1. Herbicidal Pre-Emergence Action

Seeds of monocotyledonous and dicotyledonous weed and crop plants are placed in sandy loam in wood fiber pots and covered with soil. The test compounds, formulated in the form of wettable powders (WP), are then, as an aqueous suspension with a water application rate of 600 l/ha (converted), with 0.2% of wetting agent added, applied to the surface of the covering soil.

After the treatment, the pots are placed in a greenhouse and kept under good growth conditions for the test plants. The visual assessment of the damage on the test plants is carried out after a trial period of 3 weeks by comparison with untreated controls (herbicidal activity in percent (%): 100% activity=the plants have died, 0% activity=like control plants).

2. Herbicidal Post-Emergence Action

Seeds of monocotyledonous and dicotyledonous weed and crop plants are placed in sandy loam in wood fiber pots, covered with soil and cultivated in a greenhouse under good growth conditions. 2 to 3 weeks after sowing, the test plants are treated at the one-leaf stage. The test compounds, formulated as wettable powders (WP), are then, with a water application rate of 600 l/ha (converted), with 0.2% of wetting agent added, sprayed onto the green parts of the plants. After the test plants have been kept in the greenhouse under optimum growth conditions for about 3 weeks, the activity of the preparations is rated visually in comparison to treated controls (herbicidal activity in percent (%): 100% activity=the plants have died, 0% activity=like control plants).

Applied by the pre-emergence method at 320 g of a.i./ha, the following compounds show an efficacy of ≧80% against *Avena sativa, Lolium multiflorum* and *Setaria viridis*:

I-a-2, I-a-8, I-a-9, I-a-10, I-a-11, I-a-14, I-b-10, I-b-12, I-b-13, I-b-14, I-b-15, I-b-16, I-b-21, I-b-25, I-b-27, I-b-28, I-b-33, I-b-34, I-b-36, I-b-43, I-b-44, I-b-50, I-b-52, I-b-54, I-c-1, I-c-4, I-c-5, I-c-8, I-c-9, I-c-12, I-c-14, I-e-16

Applied by the pre-emergence method at 320 g of a.i./ha, the following compounds show an efficacy of ≧80% against *Alopecurus myosuroides, Echinocloa crus-gali Lolium multiflorum* and *Setaria viridis*:

I-a-18, I-a-20, I-a-21, I-a-24, I-a-25, I-a-26, I-a-27, I-b-55, I-b-56, I-b-57, I-b-59, I-b-60, I-b-73, I-b-76, I-b-77, I-b-78, I-b-79, I-b-80, I-b-81, I-b-82, I-b-83, I-c-19, I-c-23, I-c-24, I-c-25, I-c-26, I-e-17, I-e-18

Applied by the post-emergence method at 320 g of a.i./ha, the following compounds show an efficacy of ≧80% against *Avena sativa, Lolium multiflorum* and *Setaria viridis*:

I-a-1, I-a-2, I-a-8, I-a-9, I-a-10, I-a-12, I-a-13, I-a-14, I-a-15, I-a-16, I-b-4, I-b-9, I-b-10, I-b-11, I-b-12, I-b-14, I-b-15, I-b-16, I-b-17, I-b-18, I-b-19, I-b-21, I-b-22, I-b-24, I-b-25, I-b-26, I-b-27, I-b-28, I-b-30, I-b-32, I-b-33, I-b-34, I-b-35, I-b-36, I-b-37, I-b-38, I-b-39, I-b-40, I-b-42, I-b-43, I-b-44, I-b-45, I-b-46, I-b-47, I-b-50, I-b-51, I-b-52, I-b-53, I-b-54, I-c-3, I-c-4, I-c-5, I-c-7, I-c-8, I-c-9, I-c-11, I-c-12, I-c-13, I-c-14, I-c-15, I-c-17, I-c-18, I-e-13, I-e-16.

Applied by the post-emergence method at 320 g of a.i./ha, the following compounds show an efficacy of ≧90% against *Lolium multiflorum, Setaria viridis* and *Echinocloa crus-gali*:

I-a-3, I-a-4, I-a-11, I-b-1, I-b-2, I-b-5, I-b-8, I-b-13, I-b-20, I-b-23, I-b-31, I-c-6, I-c-16, I-e-12

Applied by the post-emergence method at 80 g of a.i./ha, the following compounds show an efficacy of ≧90% against *Echinocloa crus-gali, Lolium multiflorum* and *Setaria viridis*:

I-a-18, I-a-19, I-a-22, I-a-24, I-a-25, I-a-26, I-a-27, I-b-56, I-b-57, I-b-59, I-b-62, I-b-63, I-b-66, I-b-67, I-b-68, I-b-71, I-b-72, I-b-73, I-b-74, I-b-76, I-b-77, I-b-78, I-b-79, I-b-80, I-b-81, I-b-82, I-b-83, I-c-21, I-c-22, I-c-23, I-c-25, I-c-26

Example B

Herbicidal Post-Emergence Action

Seeds of monocotyledonous and dicotyledonous weed and crop plants are placed into sandy loam in wood fiber pots or in plastic pots, covered with soil and cultivated in a greenhouse, during the vegetation period also outdoors outside of the greenhouse, under good growth conditions. 2 to 3 weeks after sowing, the test plants are treated at the one- to three-leaf stage. The test compounds, formulated as wettable powders (WP) or liquid (EC), are, in various dosages at a water application rate of 300 l/ha (converted), with wetting agent (0.2 to 0.3%) added, sprayed onto the plants and the surface of the soil. 3 to 4 weeks after the treatment of the test plants, the effect of the preparations is rated visually in comparison to untreated controls (herbicidal effect in percent (%): 100% effect=the plants have died, 0% effect=like control plants).

Use of Safeners

If it is additionally to be tested as to whether safeners can improve the plant compatibility of test substances in the case of crop plants, the following options are used for applying the safener:

- seeds of the crop plants are, before sowing, dressed with the safener substance (the amount of safener stated in percent, based on the weight of the seed)
- before the application of the test substances, the crop plants are sprayed with the safener at a certain application rate per hectare (usually 1 day before the application of the test substances)
- the safener is applied together with the test substance as a tank mix (the amount of safener is stated in g/ha or as a ratio, based on the herbicide).

By comparing the effect of test substances on crop plants without or with safener treatment, it is possible to assess the effect of the safener substance.

Container Trials with Cereal in the Greenhouse

Mefenpyr 1 Day Prior to Herbicide Application

TABLE

| | Application rate g of a.i./ha | 28 days after application | |
|---|---|---|---|
| | | Summer barley observed (%) | Summer wheat observed (%) |
| Ex. I-b-21 | 100 | 95 | |
| | 50 | 50 | 70 |
| | 25 | 30 | 60 |
| | 12.5 | 5 | 20 |
| Ex. I-b-21 + mefenpyr | 100 + 100 | 40 | |
| | 50 + 100 | 30 | 30 |
| | 25 + 100 | 3 | 5 |
| | 12.5 + 100 | 0 | 5 |

TABLE

| | Application rate g of a.i./ha | 28 days after application | |
|---|---|---|---|
| | | Summer barley observed (%) | Summer wheat observed (%) |
| Ex. I-b-15 | 100 | 90 | 85 |
| | 50 | 30 | 50 |
| | 25 | 10 | 30 |
| | 12.5 | | 10 |
| Ex. I-b-15 + mefenpyr | 100 + 100 | 20 | 20 |
| | 50 + 100 | 10 | 10 |
| | 25 + 100 | 5 | 5 |
| | 12.5 + 100 | | 0 |

TABLE

| | Application rate g of a.i./ha | 28 days after application | |
|---|---|---|---|
| | | Summer barley observed (%) | Summer wheat observed (%) |
| Ex. I-c-4 | 100 | 80 | 95 |
| | 50 | 30 | 90 |
| | 25 | 10 | 20 |
| | 12.5 | 5 | 10 |
| Ex. I-c-4 + mefenpyr | 100 + 100 | 30 | 30 |
| | 50 + 100 | 10 | 10 |
| | 25 + 100 | 5 | 5 |
| | 12.5 + 100 | 0 | 0 |

TABLE

| | Application rate g of a.i./ha | 28 days after application | |
|---|---|---|---|
| | | Summer barley observed (%) | Summer wheat observed (%) |
| Ex. I-a-1 | 100 | | 50 |
| | 50 | 70 | 50 |
| | 25 | 50 | 40 |
| | 12.5 | 5 | 10 |
| Ex. I-a-1 + mefenpyr | 100 + 100 | | 15 |
| | 50 + 100 | 20 | 5 |
| | 25 + 100 | 5 | 5 |
| | 12.5 + 100 | 5 | 2 |

TABLE

| | Application rate g of a.i./ha | 28 days after application | |
|---|---|---|---|
| | | Summer barley observed (%) | Summer wheat observed (%) |
| Ex. I-b-28 | 50 | 75 | 80 |
| | 25 | 30 | 70 |
| | 12.5 | 20 | 10 |
| Ex. I-b-28 + mefenpyr | 50 + 100 | 15 | 20 |
| | 25 + 100 | 10 | 0 |
| | 12.5 + 100 | 0 | 0 |

TABLE

| | Application rate g of a.i./ha | 28 days after application | |
|---|---|---|---|
| | | Summer barley observed (%) | Summer wheat observed (%) |
| Ex. I-b-26 | 100 | 80 | 70 |
| | 50 | 20 | 15 |
| Ex. I-b-26 + mefenpyr | 100 + 100 | 15 | 10 |
| | 50 + 100 | 10 | 0 |

TABLE

| | Application rate g of a.i./ha | 28 days after application | |
|---|---|---|---|
| | | Summer barley observed (%) | Summer wheat observed (%) |
| Ex. I-b-27 | 100 | 50 | 70 |
| | 50 | 20 | 40 |
| | 25 | | 20 |
| | 12.5 | | 10 |
| Ex. I-b-27 + mefenpyr | 100 + 100 | 15 | 30 |
| | 50 + 100 | 10 | 10 |
| | 25 + 100 | | 5 |
| | 12.5 + 100 | | 0 |

TABLE

| | Application rate g of a.i./ha | 28 days after application | |
|---|---|---|---|
| | | Summer barley observed (%) | Summer wheat observed (%) |
| Ex. I-c-9 | 100 | 90 | 70 |
| | 50 | 40 | 60 |
| | 25 | 20 | 30 |
| | 12.5 | 10 | 10 |
| Ex. I-c-9 + mefenpyr | 100 + 100 | 5 | 15 |
| | 50 + 100 | 5 | 5 |
| | 25 + 100 | 0 | 5 |
| | 12.5 + 100 | 0 | 0 |

TABLE

| | Application rate g of a.i./ha | 28 days after application | |
|---|---|---|---|
| | | Summer barley observed (%) | Summer wheat observed (%) |
| Ex. I-a-9 | 100 | | 60 |
| | 50 | 50 | 60 |
| | 25 | 20 | 5 |
| Ex. I-a-9 + mefenpyr | 100 + 100 | | 0 |
| | 50 + 100 | 20 | 0 |
| | 25 + 100 | 5 | 0 |

TABLE

|  | Application rate g of a.i./ha | 28 days after application | |
|---|---|---|---|
|  |  | Summer barley observed (%) | Summer wheat observed (%) |
| Ex. I-b-13 | 50 | 90 | 85 |
|  | 25 | 20 | 70 |
|  | 12.5 | 10 | 20 |
| Ex. I-b-13 + mefenpyr | 50 + 100 | 10 | 30 |
|  | 25 + 100 | 0 | 0 |
|  | 12.5 + 100 | 0 | 0 |

TABLE

|  | Application rate g of a.i./ha | 28 days after application | |
|---|---|---|---|
|  |  | Summer barley observed (%) | Summer wheat observed (%) |
| Ex. I-b-25 | 100 | 95 | 70 |
|  | 50 | 40 | 50 |
|  | 25 |  | 10 |
| Ex. I-b-25 + mefenpyr | 100 + 100 | 30 | 30 |
|  | 50 + 100 | 20 | 10 |
|  | 25 + 100 |  | 0 |

TABLE

|  | Application rate g of a.i./ha | 28 days after application | |
|---|---|---|---|
|  |  | Summer barley observed (%) | Summer wheat observed (%) |
| Ex. I-c-14 | 50 | 93 | 95 |
|  | 25 | 30 | 80 |
|  | 12.5 |  | 20 |
| Ex. I-c-14 + mefenpyr | 50 + 100 | 30 | 30 |
|  | 25 + 100 | 20 | 10 |
|  | 12.5 + 100 |  | 0 |

TABLE

|  | Application rate g of a.i./ha | 10 days after application Summer wheat observed (%) |
|---|---|---|
| Ex. I-b-11 | 100 | 50 |
|  | 50 | 30 |
| Ex. I-b-11 + mefenpyr | 100 + 100 | 5 |
|  | 50 + 100 | 3 |

TABLE

|  | Application rate g of a.i./ha | 10 days after application | |
|---|---|---|---|
|  |  | Summer barley observed (%) | Summer wheat observed (%) |
| Ex. I-b-16 | 100 | 60 | 60 |
|  | 50 | 40 | 50 |
|  | 25 | 20 | 20 |
| Ex. I-b-16 + mefenpyr | 100 + 100 | 20 | 10 |
|  | 50 + 100 | 10 | 5 |
|  | 25 + 100 | 5 | 0 |

TABLE

|  | Application rate g of a.i./ha | 10 days after application | |
|---|---|---|---|
|  |  | Summer barley observed (%) | Summer wheat observed (%) |
| Ex. I-b-24 | 200 | 60 | 70 |
|  | 100 | 50 | 65 |
|  | 50 | 20 | 60 |
|  | 25 |  | 30 |
| Ex. I-b-24 + mefenpyr | 200 + 100 | 10 | 5 |
|  | 100 + 100 | 5 | 3 |
|  | 50 + 100 | 5 | 3 |
|  | 25 + 100 |  | 3 |

TABLE

|  | Application rate g of a.i./ha | 10 days after application | |
|---|---|---|---|
|  |  | Summer barley observed (%) | Summer wheat observed (%) |
| Ex. I-c-8 | 100 | 30 | 80 |
|  | 50 | 20 | 70 |
|  | 25 | 15 | 50 |
| Ex. I-c-8 + mefenpyr | 100 + 100 | 0 | 5 |
|  | 50 + 100 | 0 | 3 |
|  | 25 + 100 | 0 | 0 |

TABLE

|  | Application rate g of a.i./ha | 10 days after application Summer barley observed (%) | 28 days after application Summer wheat observed (%) |
|---|---|---|---|
| Ex. I-a-3 | 50 | 20 | 25 |
|  | 25 | 15 | 25 |
| Ex. I-a-3 + mefenpyr | 50 + 100 | 0 | 0 |
|  | 25 + 100 | 0 | 0 |

TABLE

|  | Application rate g of a.i./ha | 10 days after application Summer wheat observed (%) |
|---|---|---|
| Ex. I-b-33 | 100 | 65 |
|  | 50 | 30 |
|  | 25 | 15 |
| Ex. I-b-33 + mefenpyr | 100 + 100 | 30 |
|  | 50 + 100 | 15 |
|  | 25 + 100 | 5 |

TABLE

|  | Application rate g of a.i./ha | 10 days after application | |
|---|---|---|---|
|  |  | Summer barley observed (%) | Summer wheat observed (%) |
| Ex. I-a-15 | 100 | 30 | 30 |
|  | 50 | 20 | 20 |
| Ex. I-a-15 + mefenpyr | 100 + 100 | 15 | 10 |
|  | 50 + 100 | 5 | 5 |

| | | 10 days after application | |
|---|---|---|---|
| | Application rate g of a.i./ha | Summer barley observed (%) | Summer wheat observed (%) |
| Ex. I-b-44 | 100 | 40 | 40 |
| | 50 | 40 | 40 |
| | 25 | 20 | 20 |
| Ex. I-b-44 + mefenpyr | 100 + 100 | 10 | 10 |
| | 50 + 100 | 10 | 10 |
| | 25 + 100 | 5 | 5 |

| | | 28 days after application | |
|---|---|---|---|
| | Application rate g of a.i./ha | Summer barley observed (%) | Summer wheat observed (%) |
| Ex. I-c-10 | 100 | 90 | 85 |
| | 50 | 50 | 80 |
| | 25 | 25 | 40 |
| Ex. I-c-10 + mefenpyr | 100 + 100 | 20 | 50 |
| | 50 + 100 | 10 | 20 |
| | 25 + 100 | 5 | 3 |

| | | 10 days after application | |
|---|---|---|---|
| | Application rate g of a.i./ha | Summer barley observed (%) | Summer wheat observed (%) |
| Ex. I-b-42 | 100 | 50 | 50 |
| | 50 | 40 | 50 |
| | 25 | 20 | 40 |
| Ex. I-b-42 + mefenpyr | 100 + 100 | 5 | 20 |
| | 50 + 100 | 0 | 10 |
| | 25 + 100 | 0 | 5 |

| | | 10 days after application | |
|---|---|---|---|
| | Application rate g of a.i./ha | Summer barley observed (%) | Summer wheat observed (%) |
| Ex. I-a-13 | 100 | 60 | 80 |
| | 50 | 50 | 80 |
| | 25 | 30 | 50 |
| Ex. I-a-13 + mefenpyr | 100 + 100 | 15 | 30 |
| | 50 + 100 | 15 | 20 |
| | 25 + 100 | 10 | 10 |

| | | 28 days after application | |
|---|---|---|---|
| | Application rate g of a.i./ha | Summer barley observed (%) | Summer wheat observed (%) |
| Ex. I-a-18 | 100 | 90 | 80 |
| | 50 | 50 | 70 |
| | 25 | 20 | 60 |
| Ex. I-a-18 + mefenpyr | 100 + 100 | 10 | 20 |
| | 50 + 100 | 7 | 10 |
| | 25 + 100 | 5 | 5 |

| | | 10 days after application | |
|---|---|---|---|
| | Application rate g of a.i./ha | Summer barley observed (%) | Summer wheat observed (%) |
| Ex. I-b-23 | 100 | 60 | 80 |
| | 50 | 60 | 70 |
| | 25 | 30 | 40 |
| | 12.5 | | 30 |
| Ex. I-b-23 + mefenpyr | 100 + 100 | 40 | 50 |
| | 50 + 100 | 20 | 30 |
| | 25 + 100 | 10 | 10 |
| | 12.5 + 100 | | 0 |

Compared to the known compounds from I-6-a-1 and I-6-b-1 from WO 01/74780*, the compounds according to the invention, for example, show considerably better activity when applied by the post-emergence method

| Example | g/ha | ALOMY | AVEFA | LOLMU |
|---|---|---|---|---|
| I-6-a-1* | 200 | 30 | 10 | 30 |
| | 100 | 10 | 0 | 30 |
| I-a-9 | 200 | 98 | 100 | 99 |
| | 100 | 98 | 100 | 99 |
| I-6-b-1* | 200 | 20 | 20 | 40 |
| | 100 | 0 | 0 | 20 |
| I-b-26 | 200 | 97 | 98 | 100 |
| | 100 | 95 | 98 | 70 |
| I-b-24 | 200 | 90 | 95 | 98 |
| | 100 | 80 | 90 | 95 |

Example C

| *Myzus* test (MYZUPE spray treatment) | |
|---|---|
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 500 g/ha, an efficacy of ≧90%:

I-a-2, I-a-3, I-a-18, I-a-20, I-a-22, I-b-1, I-b-14, I-b-15, I-b-16, I-b-17, I-b-18, I-b-21, I-b-22, I-b-25, I-b-51, I-b-52, I-b-

55, I-b-56, I-b-57, I-b-58, I-b-59, I-b-60, I-b-61, I-b-63, I-b-67, I-b-71, I-b-72, I-c-1, I-c-4, I-c-5, I-c-7, I-c-19, I-c-22.

Example D

| *Tetranychus* test; OP resistant/spray treatment (TETRUR) | |
|---|---|
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Disks of bean leaves (*Phaseolus vulgaris*) which are infested by all stages of the greenhouse red spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 100 g/ha, an efficacy of ≧90%:

I-a-1, I-a-2, I-a-3, I-a-11, I-a-18, I-a-20, I-a-22, I-a-23, I-b-1, I-b-9, I-b-10, I-b-11, I-b-14, I-b-15, I-b-17, I-b-18, I-b-19, I-b-21, I-b-23, I-b-25, I-b-26, I-b-29, I-b-30, I-b-31, I-b-35, I-b-37, I-b-55, I-b-56, I-b-57, I-b-58, I-b-59, I-b-60, I-b-64, I-b-67, I-b-70, I-b-75, I-b-76, I-b-77, I-b-78, I-b-79, I-b-80, I-b-83, I-b-42, I-c-3, I-c-4, I-c-5, I-c-10, I-c-19, I-c-22, I-c-24, I-c-25, I-c-27, I-e-17.

Example E

| Phaedon test (PHAECO spray treatment) | |
|---|---|
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 500 g/ha, an efficacy of ≧80%:

I-a-1, I-a-2, I-a-3, I-a-15, I-a-20, I-a-21, I-a-22, I-b-14, I-b-15, I-b-16, I-b-17, I-b-18, I-b-19, I-b-21, I-b-22, I-b-55, I-b-61, I-b-67, I-b-71, I-c-1, I-c-4, I-c-5, I-c-19, I-c-22.

Example F

| *Boophilus microplus* test (BOOPMI injection) | |
|---|---|
| Solvent: | Dimethyl sulphoxide |

To produce a suitable preparation of active compound, 1 part by weight of active compound is mixed with the stated amount of solvent and emulsifier, and the concentrate is diluted with emulsifier-containing water to the desired concentration.

The solution of active compound is injected into the abdomen (*Boophilus microplus*) and the animals are transferred into dishes and stored in a climatized room.

After the desired period of time, the effect in % is determined. In this case 100% means that none of the ticks has laid fertile eggs.

In this test, for example, the following compounds of the Preparation Examples show, at an application rate of 20 µg/animal, an efficacy of ≧90%:

I-b-10, I-b-55, I-b-70, I-c-10, I-c-22.

Example G

| Critical concentration test/soil insects - treatment of transgenic plants | |
|---|---|
| Test insect: | *Diabrotica balteata* - larvae in the soil |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example H

| *Heliothis virescens* test - treatment of transgenic plants | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

The invention claimed is:

1. A compound of the formula (I)

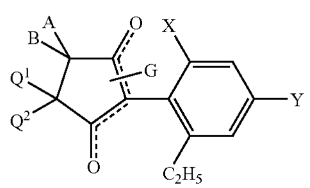

(I)

in which

X represents methyl,

Y represents methyl, or

X and Y both represent ethyl,

A represents methyl,

B represents hydrogen or methyl or

A, B and the carbon atom to which they are attached represent saturated $C_5$-$C_6$-cycloalkyl in which optionally one ring member is replaced by oxygen and which is optionally monosubstituted by methyl, A and $Q^1$ together represent $C_3$-$C_5$-alkanediyl or $C_3$-$C_5$-alkenediyl, each of which is optionally monosubstituted by methyl, which optionally contain one of the groups below 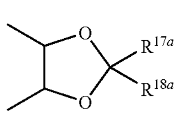 $Q^1$ and $Q^2$ independently of one another represent hydrogen, or X represents ethyl and Y represents methyl and a) A, B and the carbon atom to which they are attached represent saturated $C_5$-$C_6$-cycloalkyl in which optionally one ring member is replaced by oxygen, $Q^1$ and $Q^2$ represent hydrogen or b) A and $Q^1$ together represent $C_3$-$C_5$-alkanediyl or $C_3$-$C_5$-alkenediyl, each of which is optionally monosubstituted by methyl, which optionally contain one of the groups below or is interrupted or bridged by an oxygen atom, B and $Q^2$ independently of one another represent hydrogen, G represents hydrogen (a) or represents one of the groups (b)

(c)

(e)

in which

L represents oxygen and

M represents oxygen, $R^1$ represents $C_1$-$C_6$-alkyl, $C_1$-$C_2$-alkoxy-$C_1$-$C_2$-alkyl, or represents $C_1$-$C_4$-alkyl which is monosubstituted by chlorine, $R^2$ represents $C_1$-$C_8$-alkyl, $R^4$ represents $C_1$-$C_4$-alkoxy which is optionally monosubstituted by chlorine, $R^5$ represents $C_1$-$C_4$-alkoxy which is optionally monosubstituted by chlorine, $R^{17a}$ and $R^{18a}$ represent methyl.

2. A process for preparing a compound of the formula (I) as claimed in claim 1 to obtain (A) a compound of the formula (I-a)

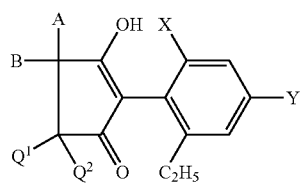

(I-a)

comprising cyclizing intremolecularly a ketocarboxylic ester of the formula (II)

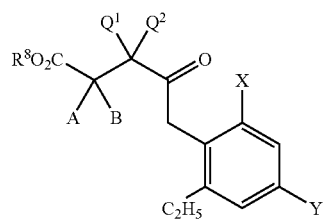

(II)

in which
$R^8$ represents alkyl,
if appropriate in the presence of a diluent and in the presence of a base.

3. A composition comprising an effective amount of an active compound combination comprising, as components, a') at least one compound of the formula (I) of claim 1 and (b') at least one crop plant compatibility-improving compound selected from the group consisting of:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy) propionic acid (mecoprop), diethyl 1-(2,4-dichorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoyl)-4-[(methylaminocarbonyl)amino] benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzenesulphonamide, and/or one of the following compounds, of the formula (IIa)

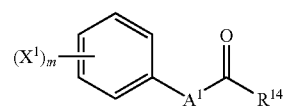

(IIa)

or of the formula (IIb)

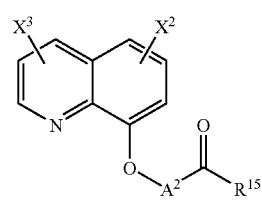

(IIb)

or of the formula (IIc)

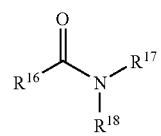

(IIc)

where m represents a number 0, 1, 2, 3, 4 or 5, $A^1$ represents one of the divalent heterocyclic groupings shown below

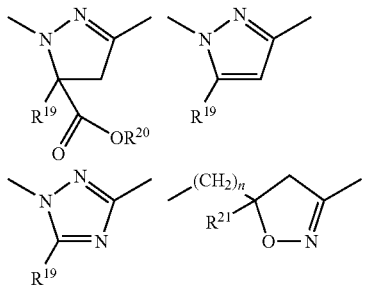

n represents a number 0, 1, 2, 3, 4 or 5, $A^2$ represents optionally $C_1$-$C_4$-alkyl- and/or $C_1$-$C_4$-alkoxy-carbonyl- and/or $C_1$-$C_4$-alkenyloxycarbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, of the formula (IId)

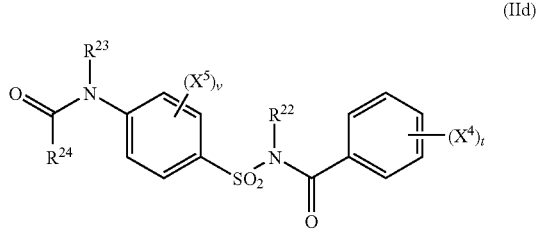

(IId)

or of the formula (IIe)

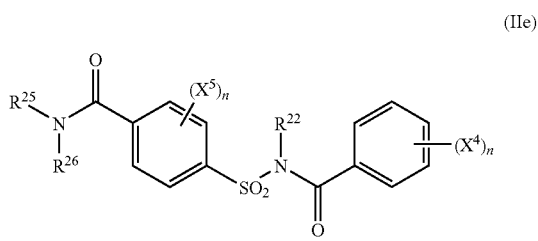

(IIe)

where t represents a number 0, 1, 2, 3, 4 or 5, v represents a number 0, 1 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

4. The composition as claimed in claim 3 in which the crop plant compatibility-improving compound is selected from the group consisting of:
cloquintocet-mexyl, fenchlorazole-ethyl, isoxadifen-ethyl, mefenpyr-diethyl, furilazole, fenclorim, cumyluron, dymron or the compounds

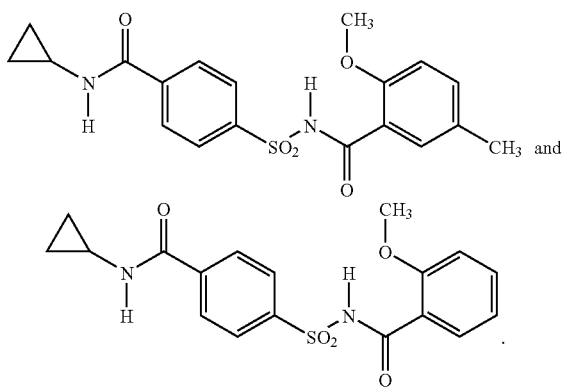

5. The composition as claimed in claim 3 in which the crop plant compatibility-improving compound is cloquintocet-mexyl.

6. The composition as claimed in claim 3 in which the crop plant compatibility-improving compound is mefenpyr-diethyl.

7. A method for preparing a pesticide and/or herbicide comprising utilizing a compound as claimed in claim 5.

8. A pesticide and/or herbicide comprising at least one compound of the formula (I) as claimed in claim 1.

9. A method for controlling insects, arachnids, helminths, nematodes and/or unwanted vegetation, comprising allowing a compound of the formula (I) as claimed in claim 1 to act on a pest and/or a habitat thereof.

10. A method for controlling a insects, arachnids, helminths, nematodes and/or unwanted vegetation comprising utilizing a compound of claim 1.

11. A process for preparing pesticide and/or herbicide, comprising mixing a compound of the formula (I) as claimed in claim 1 with an extender and/or surfactant.

12. A method for controlling unwanted vegetation, comprising allowing a composition as claimed in claim 3 to act on a plant or a surrounding thereof.

13. A method for controlling unwanted vegetation comprising using a composition as claimed in claim 3.

14. A method of controlling unwanted vegetation, comprising causing a compound of the formula (I) as claimed in claim 1 to act, separately in close temporal succession, on a plant or a surrounding thereof.

15. A compound of formula (I) according to claim 1, wherein the compound has the structure of formula

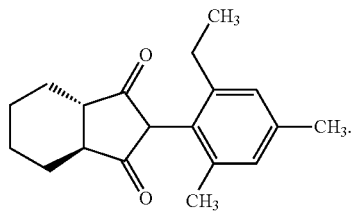

16. A compound of formula (I) according to claim 1, in which:
X and Y both represents ethyl;
G represents hydrogen;
A and $Q^1$ together represents —$(CH_2)_4$—; and
B and $Q^2$ independently of one another represent hydrogen.

17. A compound of formula (I) according to claim 1, in which:
X represents ethyl;
Y represents methyl;
G represents hydrogen;
A and $Q^1$ together represents —$(CH_2)_4$—; and
B and $Q^2$ independently of one another represent hydrogen.

* * * * *